United States Patent [19]
Bock et al.

[11] Patent Number: 5,756,504
[45] Date of Patent: *May 26, 1998

[54] TOCOLYTIC OXYTOCIN RECEPTOR ANTAGONISTS

[75] Inventors: Mark G. Bock, Hatfield; Ben E. Evans, Lansdale; J. Christopher Culberson, Hatfield; Kevin F. Gilbert, Bechtelsville; Kenneth E. Rittle, Green Lane; Peter D. Williams, Harleysville, all of Pa.

[73] Assignee: Merck & Co., Inc., Rahway, N.J.

[*] Notice: The term of this patent shall not extend beyond the expiration date of Pat. No. 5,464,788.

[21] Appl. No.: 718,415

[22] PCT Filed: Mar. 23, 1995

[86] PCT No.: PCT/US95/03738

§ 371 Date: Sep. 23, 1996

§ 102(e) Date: Sep. 23, 1996

[87] PCT Pub. No.: WO95/25443

PCT Pub. Date: Sep. 28, 1995

Related U.S. Application Data

[63] Continuation-in-part of Ser. No. 217,270, Mar. 24, 1994, Pat. No. 5,464,788.

[51] Int. Cl.[6] ............ A61K 31/495; C07D 241/04; C07D 401/12; C07D 403/12
[52] U.S. Cl. ............ 514/252; 514/253; 514/255; 514/278; 544/121; 544/295; 544/357; 544/360; 544/364; 544/366; 544/367; 544/370; 544/372; 544/373; 544/374; 544/383; 544/386; 544/387; 544/388; 544/390; 544/391; 546/17
[58] Field of Search ............ 544/360, 364, 544/370, 295, 357, 373, 383, 386, 387, 388, 389, 390, 391, 372; 514/252, 253, 255

[56] References Cited

U.S. PATENT DOCUMENTS

| | | | |
|---|---|---|---|
| 3,173,917 | 3/1965 | Starker et al. | 544/392 |
| 3,198,799 | 8/1965 | Regnier et al. | 544/392 |
| 4,087,425 | 5/1978 | Garcia et al. | 514/414 |
| 4,147,870 | 4/1979 | Garcia et al. | 544/383 |
| 4,894,386 | 1/1990 | Brown et al. | 514/414 |

(List continued on next page.)

FOREIGN PATENT DOCUMENTS

| | | |
|---|---|---|
| 0 384 843 | 8/1990 | European Pat. Off. . |
| 0 450 761 | 10/1991 | European Pat. Off. . |
| 0 470 514 | 2/1992 | European Pat. Off. . |

(List continued on next page.)

OTHER PUBLICATIONS

Boissier et al, *J. Med. Chem.* vol. 6(5), pp. 541–544 (1963).
Boissier et al, *Chemical Abstract* vol. 59, No. 128046 (1963).

D.J. Pettibone, et al., Drug. Dev. Res. (1993) 30, 129–142, entitled L–368, 899, A Potent Orally Active Oxytocin Antagonist for Potential Use in Preterm Labor.

(List continued on next page.)

*Primary Examiner*—Emily Bernhardt
*Attorney, Agent, or Firm*—Melvin Winokur

[57] ABSTRACT

Compounds of the formula X—Y—R, or the pharmaceutically acceptable salts and esters thereof, wherein X is

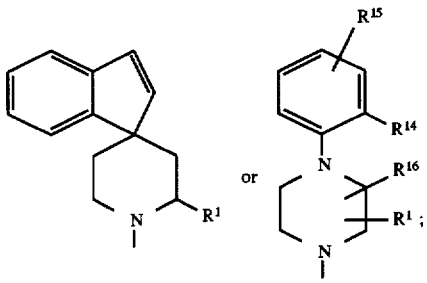

Y is —$SO_2$—, —$(CH_2)_p$— or —CO—$(CH_2)_p$—; R is unsubstituted or substituted phenyl where said substitutents are one or more of $R^5$, $R^6$ or $R^7$; $R^1$ is hydrogen, cyano, phenyl, —$CONHR^2$, —$CONR^2R^2$, —$(CH_2)_m$—$OR^2$, —$(CH_2)_p$—$S(O)_r$—$R^2$, —$(CH_2)_m$—$CO_2R^2$, —$(CH_2)_m$—$N_3$, —$(CH_2)_m$—$NH_2$ or —$(CH_2)_m$—$NR^2R^2$; $R^2$ is hydrogen, $C_{3-8}$ cycloalkyl or $C_{1-5}$ alkyl; $R^5$ and $R^6$ are each independently selected from hydrogen, $C_{1-5}$ alkoxy, halogen or —$(CH_2)_n$—$N(R^2)$—$C(O)$—$R^{18}$; $R^7$ is hydrogen or

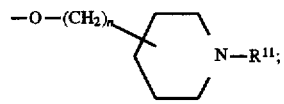

$R^{11}$ is selected from hydrogen, $C_{1-5}$ alkyl-carbonyl, —Z—$R^{13}$,

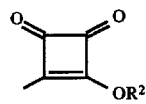

or substituted $C_{1-5}$ alkyl wherein said alkyl substituent is unsubstituted, mono-, di- or tri-substituted pyridyl wherein said substitutents on said pyridyl are independently selected from halogen, $C_{1-5}$ alkyl or $C_{1-5}$ alkoxyl; $R^{13}$ is unsubstituted or substituted $C_{1-10}$ alkyl wherein the substituent is selected from —$N(R^2)_2$, —$NHR^2$ or imidazolyl; $R^{14}$ and $R^{15}$ are each independently selected from $C_{1-5}$ alkyl, $C_{1-5}$ alkoxy or halogen; $R^{16}$ is hydrogen or oxo; $R^{18}$ is $C_{1-5}$ alkoxyl, unsubstituted or substituted $C_{1-5}$ alkyl where said substituent is Het, unsubstituted or substituted $C_{2-5}$ alkenyl where said subsituent is Het or Het; Het is benzimidazolyl, carboxymethyl-substituted benzimidazolyl or indolyl; m is an integer of from 1 to 5; p is an integer of from 1 to 3; and r is an integer of from 0 to 2. Such compounds as useful as oxytocin and vasopressin receptor antagonists.

11 Claims, No Drawings

U.S. PATENT DOCUMENTS

| | | | |
|---|---|---|---|
| 5,091,387 | 2/1992 | Evans et al. | 514/278 |
| 5,204,349 | 4/1993 | Bock et al. | 514/253 |
| 5,356,904 | 10/1994 | Freidinger et al. | 514/312 |
| 5,464,788 | 11/1995 | Bock et al. | 514/252 |
| 5,663,341 | 9/1997 | Rossen et al. | 544/388 |
| 5,665,719 | 9/1997 | Bock et al. | 514/227.8 |
| 5,670,509 | 9/1997 | Evans et al. | 514/278 |

FOREIGN PATENT DOCUMENTS

| | | |
|---|---|---|
| 0 486 280 | 5/1992 | European Pat. Off. . |
| 0 532 097 | 3/1993 | European Pat. Off. . |
| 0 533 240 | 3/1993 | European Pat. Off. . |
| 0 533 241 | 3/1993 | European Pat. Off. . |
| 0 533 242 | 3/1993 | European Pat. Off. . |
| 0 533 243 | 3/1993 | European Pat. Off. . |
| 2081346 | 12/1970 | France . |
| 2 292 477 | 10/1975 | France . |
| WO95/02405 | 1/1995 | WIPO . |
| WO95/02587 | 1/1995 | WIPO . |

OTHER PUBLICATIONS

B.E. Evans, et al., J. Med. Chem. (1993) 36, 3993–4005, entitled Nanomolar–Affinity, Non–Peptide Oxytocin Receptor Antagonists.

M.G. Bock, et al., Vasopressin (1993), J. Libbey Eurotext, pp. 539–547.

P.D. Williams, et al., J. Med. Chem. (1994) 37, 565–571.

D.J. Pettibone, et al., Reg. Peptides (1993), 45, 289–293, entitled Development and Pharmacological.

B.E. Evans, et al., J. Med. Chem. (1992) 35, 3919–3927, entitled Orally Active, Non–Peptide oxytocin Antagonists.

D.J. Pettidone, et al., J. Pharm. Exp. Ther. (1992) 264, 308–314, entitled Identification of an Orally Active, Non–Peptide Oxytocin Antagonist.

TOCOLYTIC OXYTOCIN RECEPTOR ANTAGONISTS

This application is a 371 application of PCT/US95/03738 filed Mar. 23, 1995 which is a continuation-in-part of U.S. Ser. No. 08/217,270, filed Mar. 24, 1994, now U.S. Pat. No. 5,464,788, issued Nov. 7, 1995.

FIELD OF THE INVENTION

The present invention provides novel compounds, novel compositions, methods of their use and methods of their manufacture, such compounds are generally pharmacologically useful as agents in obstetric and gynecologic therapy. The aforementioned pharmacologic activities are useful in the treatment of mammals. More specifically, the compounds of the present invention can be used in the treatment of preterm labor, stopping labor preparatory to Caesarean delivery, and in the treatment of dysmenorrhea. At the present time, there is a need in the area of obstetric and gynecologic therapy for such agents.

BACKGROUND OF THE INVENTION

In the field of obstetrics, one of the most important problems is the management of preterm labor. A significant number of the pregnancies progressing past 20 weeks of gestation experience premature labor and delivery, which is a leading cause of neonatal morbidity and mortality. Despite major advances in neonatal care, retention of the fetus in utero is preferred in most instances.

Tocolytic (uterine-relaxing) agents that are currently in use include $\beta_2$-adrenergic agonists, magnesium sulfate and ethanol. Ritodrine, the leading $\beta_2$-adrenergic agonist, causes a number of cardiovascular and metabolic side effects in the mother, including tachycardia, increased renin secretion, hyperglycemia (and reactive hypoglycemia in the infant). Other $\beta_2$-adrenergic agonists, including terbutaline and albuterol have side effects similar to those of ritodrine. Magnesium sulfate at plasma concentrations above the therapeutic range of 4 to 8 mg/dL can cause inhibition of cardiac conduction and neuromuscular transmission, respiratory depression and cardiac arrest, thus making this agent unsuitable when renal function is impaired. Ethanol is as effective as ritodrine in preventing premature labor, but it does not produce a corresponding reduction in the incidence of fetal respiratory distress that administration of ritodrine does.

It has been proposed that a selective oxytocin antagonist would be the ideal tocolytic agent. In the last few years, evidence has accumulated to strongly suggest that the hormone oxytocin may be a physiological initiator of labor in several mammalian species including humans. Oxytocin is believed to exert this effect in part by directly contracting the uterine myometrium and in part by enhancing the synthesis and release of contractile prostaglandins from the uterine endometrium/decidua. These prostaglandins may, in addition, be important in the cervical ripening process. By these mechanisms, the process of labor (term and preterm) is initiated by a heightened sensitivity of the uterus to oxytocin, resulting in part as a result of a well-documented increase in the number of oxytocin receptors in this tissue. This "up-regulation" of oxytocin receptors and enhanced uterine sensitivity appears to be due to trophic effects of rising plasma levels of estrogen towards term. By blocking oxytocin, one would block both the direct (contractile) and indirect (enhanced prostaglandin synthesis) effects of oxytocin on the uterus. A selective oxytocin blocker, or antagonist, would likely be more efficacious for treating preterm labor than current regimens. In addition, since oxytocin at term has major effects only on the uterus, such an oxytocin antagonizing compound would be expected to have few, if any, side effects.

The compounds of the present invention can also be useful in the treatment of dysmenorrhea. This condition is characterized by cyclic pain associated with menses during ovulatory cycles. The pain is thought to result from uterine contractions and ischemia, probably mediated by the effect of prostaglandins produced in the secretory endometrium. By blocking both the direct and indirect effects of oxytocin on the uterus, a selective oxytocin antagonist can be more efficacious for treating dysmenorrhea than current regimens. An additional use for the present invention is for the stoppage of labor preparatory to Caesarean delivery.

It is, therefore, a purpose of this invention to provide substances which more effectively antagonize the function of oxytocin in disease states in animals, preferably mammals, especially in humans. It is another purpose of this invention to prepare novel compounds which more selectively inhibit oxytocin. It is still another purpose of this invention to provide a method of antagonizing the functions of oxytocin in disease states in mammals. It is also a purpose of this invention to develop a method of preventing or treating oxytocin-related disorders of preterm labor and dysmenorrhea by antagonizing oxytocin.

It has now been found that compounds of the present invention are antagonists of oxytocin and bind to the oxytocin receptor.

When the oxytocin receptor is bound by the compounds of the present invention, oxytocin is antagonized by being blocked from its receptor and thus being unable to exert its biologic or pharmacologic effects.

These compounds are useful in the treatment and prevention of oxytocin-related disorders of animals, preferably mammals and especially humans. These disorders are primarily preterm labor and dysmenorrhea. The compounds would also find usefulness for stoppage of labor preparatory to Caesarean delivery. Additionally, such compounds are useful in inducing contraception in mammals inasmuch as oxytocin antagonists have now been shown to inhibit the release of oxytocin-stimulated luteinizing hormone (LH) by anterior pituitary cells.

Compounds of the present invention are also inhibitors of vasopressin and can bind to the vasopressin receptor. These compounds are useful in inducing vasodilation, treating hypertension, inducing diuresis and inhibiting platelet agglutination.

SUMMARY OF THE INVENTION

The compounds and their pharmaceutically acceptable salts and esters of the present invention are of the general formula X—Y—R, wherein X is

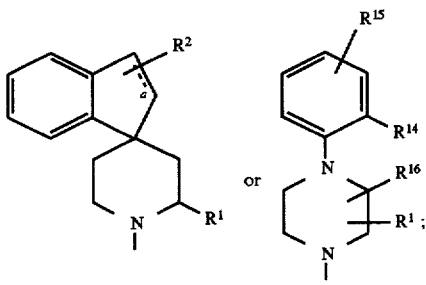

a is a single or double bond;

Y is selected from the group consisting of —COO—, —CONR$^2$—, —C(=NR$^2$)—, —SO$_2$—, —CO—(CH$_2$)$_n$—, —(CH$_2$)$_p$— and —(CH$_2$)$_p$—CO—;

R is selected from the group consisting of furyl, thienyl, pyrrolyl, napthyl, indolyl, benzimidazolyl, tetrahydronapthyl, pyridyl, quinolyl, unsubstituted or substituted cyclohexyl where said substituent is R$^4$, and unsubstituted or substituted phenyl where said substitutents are one or more of R$^5$, R$^6$ or R$^7$;

R$^1$ is selected from the group consisting of hydrogen, C$_{1-5}$ alkyl, cyano, carboxyl, phenyl, —CONHR$^2$, —CONR$^2$R$^2$, —CO$_2$R$^3$, —COR$^3$, —(CH$_2$)$_m$—OR$^2$, —(CH$_2$)$_p$—S(O)$_r$—R$^2$, —(CH$_2$)$_m$—CO$_2$R$^2$, —(CH$_2$)$_m$—N$_3$, —(CH$_2$)$_m$—NH$_2$ and —(CH$_2$)$_m$—NR$^2$R$^2$;

R$^2$ is selected from the group consisting of hydrogen, benzyl, C$_{3-8}$ cycloalkyl and C$_{1-5}$ alkyl;

R$^3$ is selected from the group consisting of C$_{1-5}$ alkyl and phenyl;

R$^4$ is selected from the group consisting of hydrogen, oxo, hydroxyl, C$_{1-5}$ alkyl and C$_{1-5}$ alkoxy;

R$^5$ and R$^6$ are each independently selected from the group consisting of hydrogen, C$_{1-5}$ alkyl, C$_{1-5}$ alkoxy, trifluoromethoxy, 2,2,2-trifluoroethoxy, allyloxy, propargyloxy, trifluoromethyl, C$_{3-8}$ cycloalkyloxy, cylopropylmethoxy, hydroxy, hydroxyalkyl, cyano, nitro, amino, halogen, —(CH$_2$)$_n$—CO—R$^{10}$, —O(CH$_2$)$_n$—CO—R$^{10}$, —(CH$_2$)$_n$—R$^{10}$, —OCH$_2$(CH$_2$)$_q$—R$^{10}$, —OCH$_2$(CH$_2$)$_q$—N(R$^2$)—R$^{17}$ and —(CH$_2$)$_n$—N(R$^2$)—R$^{17}$;

R$^7$ is selected from the group consisting of hydrogen, C$_{1-5}$ alkyl, halogenated C$_{1-5}$ alkyl, phenyl, phenyl C$_{1-5}$ alkyl, amino C$_{2-5}$ alkoxy, C$_{1-5}$ alkoxy, carboxyl, carboxy C$_{1-5}$ alkyl, C$_{1-5}$ alkoxycarbonyl, halogen, hydroxyl,

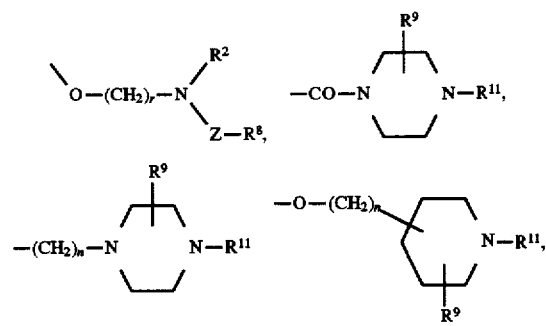

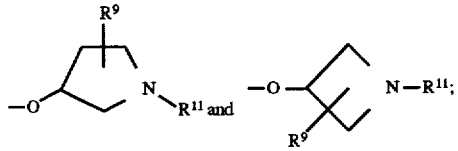

R$^8$ is selected from the group consisting of hydrogen, Het, C$_{1-5}$ alkoxyl, unsubstituted C$_{1-5}$ alkyl and substituted C$_{1-5}$ alkyl where said substitutent is selected from the group consisting of carboxyl, hydroxyl, amino, —N(R$^2$)$_2$, —NHR$^2$, C$_{1-10}$ alkoxycarbonylamino and Het;

R$^9$ is selected from the group consisting of hydrogen, C$_{1-5}$ alkyl, hydroxyalkyl, methylthioalkyl, methylsulfonylalkyl, methylsulfonyl, cyano, carbamoyl, —(CH$_2$)$_n$—CO$_2$H, —(CH$_2$)$_p$—R$^{10}$ and —(CH$_2$)$_p$—COR$^{10}$;

R$^{10}$ is selected from the group consisting of hydroxyl, C$_{1-5}$ alkoxyl, amino, —N(R$^2$)$_2$, —NHR$^2$, 1-piperazinyl, 4-methyl-1-piperazinyl, pyridinyl, 4-morpholinyl, 1-pyrrolidinyl and 1-piperidinyl;

R$^{11}$ is selected from the group consisting of hydrogen, C$_{1-5}$ alkoxycarbonyl, C$_{1-5}$ alkylcarbonyl, C$_{1-5}$ alkyl, allyl, 5-tetrazolyl, 2-pyrimidinyl, 2-pyrazinyl, 2-pyridyl, 4-pyridyl, 4-piperidinyl, 1-methyl-4-piperidinyl, 4-tetrahydropyranyl, —CO—NH—COR$^{12}$, —CO—NH—SO$_2$R$^{12}$, —SO$_2$—NH—COR$^{12}$, —Z—R$^{13}$,

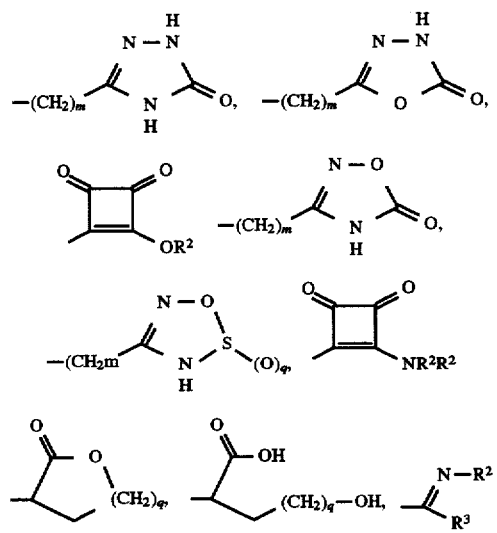

and substituted C$_{1-10}$ alkyl wherein said substituent on said alkyl is selected from the group consisting of hydroxyl, C$_{1-10}$ alkoxyl, C$_{1-10}$ alkoxycarbonyl, carboxyl, —SO$_2$NH$_2$, amino, —N(R$^2$)$_2$, —NHR$^2$, 1-piperazinyl, 4-methyl-1-piperazinyl, pyridinyl, quinolinyl, 4-morpholinyl, -1-pyrrolidinyl, imidazolyl, 4-piperidinyl, 1-methyl-4-piperidinyl, 1-piperidinyl, 5-tetrazolyl, unsubstituted, mono-, di- or tri-substituted pyridyl wherein said substituents on said pyridyl are independently selected from halogen, C$_{1-5}$ alkoxyl, alkylenedioxy, C$_{1-5}$ alkyl, C$_{1-10}$ alkoxycarbonyl, carboxyl, trifluoromethyl, —SO2CH$_3$ or —SO$_2$NH$_2$, and unsubstituted, mono-, di- or tri-substituted phenyl wherein said substituents on said phenyl are independently selected from the group consisting of halogen, $C_{1-5}$ alkoxyl, alkylenedioxy, $C_{1-5}$ alkyl, $C_{1-10}$ alkoxycarbonyl, carboxyl, trifluoromethyl, —$SO_2CH_3$, and —$SO_2NH_2$;

$R^{12}$ is selected from the group consisting of $C_{1-10}$ alkyl, trifloromethyl, and phenyl optionally substituted with one to three members of the group consisting of $C_{1-5}$ alkyl, $C_{1-10}$ alkoxyl, halogen and trifluoromethyl;

$R^{13}$ is selected from the group consisting of $C_{1-10}$ alkyl, $C_{1-10}$ alkoxyl, amino, carboxyl, phenyl, vinyl, morpholinyl, piperidinyl, pyrrolidinyl, pyridinyl, piperazinyl, 1-methyl-4-piperazinyl, 1-alkoxycarbonyl-4-piperidinyl, —$N(R^2)$—$(CH_2)_i$—$R^{10}$, substituted phenyl wherein the substituent is selected from the group consisting of nitro, $C_{1-10}$ alkoxyl, amino, monoalkylamino, dialkylamino, halogen, 1-piperazinyl, 4-piperidinyloxy, 4-methyl-1-piperazinyl, $C_{1-10}$ alkoxycarbonyl, carboxyl, amino $C_{1-10}$ alkyl, monoalkylaminoalkyl, dialkylaminoalkyl, 4-morpholinylalkyl, 1-piperazinylalkyl, and 4-methyl-1-piperazinylalkyl; and substituted $C_{1-10}$ alkyl wherein the substituent is selected from the group consisting of phenyl, hydroxyl, $C_{1-10}$ alkoxyl, $C_{1-10}$ alkoxycarbonyl, carboxyl, halogen, amino, —$N(R^2)_2$, —$NHR^2$, 1-piperazinyl, 1-methyl-4-piperazinyl, pyridinyl, 4-morpholinyl, pyrrolidinyl, imidazolyl, 5-tetrazolyl, azetidinyl, piperidinyl, and substituted phenyl wherein the substituent is selected from the group consisting of nitro, $C_{1-10}$ alkoxyl, amino, monoalkylamino, dialkylamino, halogen, 1-piperazinyl, 4-piperidinyloxy, 4-methyl-1-piperazinyl, $C_{1-10}$ alkoxycarbonyl, carboxyl, aminoalkyl, monoalkylaminoalkyl, dialkylaminoalkyl, 4-morpholinylalkyl, 1-piperazinylalkyl, and 4-methyl-1-piperazinylalkyl;

$R^{14}$ and $R^{15}$ are each independently selected from the group consisting of hydrogen, $C_{1-5}$ alkyl, $C_{1-5}$ alkoxyl, halogen, nitro and cyano;

$R^{16}$ is selected from the group consisting of hydrogen and oxo;

$R^{17}$ is selected from the group consisting of hydrogen, $R^2$ and —Z—$R^{18}$;

$R^{18}$ is selected from the group consisting of $C_{1-5}$ alkoxyl, Het, unsubstituted or substituted $C_{1-5}$ alkyl where said substituent is Het and unsubstituted or substituted $C_{2-5}$ alkenyl where said substituent is Het;

Het is selected from the group consisting of imidazolyl, piperidinyl, $C_{1-5}$ alkyl-substituted piperidinyl, piperazinyl, $C_{1-5}$ alkyl-substituted piperazinyl, benzimidazolyl, carboxymethyl-substituted benzimidazolyl, indolyl, morpholinyl, tetrazolyl, $C_{1-5}$ alkylcarbonyl-substituted piperidinyl, $C_{1-5}$ alkoxycarbonyl-substituted piperidinyl, pyrrolidinyl, $C_{1-5}$ alkyl-substituted pyrrolidinyl, and pyridinyl;

Z is —CO— or —$SO_2$—;

i is an integer of from 2 to 5;

m is an integer of from 1 to 5;

n is an integer of from 0 to 3;

p is an integer of from 1 to 3; and q is an integer of from 1 to 2;

r is an integer of from 0 to 2;

provided that when X is and Y is —$SO_2$—, —CO—$(CH_2)_n$— or —$(CH_2)_p$—; and $R^{15}$ is hydrogen, methyl or halogen; and R is thienyl, napthyl, indolyl, pyridyl, quinolyl, unsubstituted or substituted cyclohexyl where said substituent is $R^4$, or unsubstituted or substituted phenyl where said substituents are one or more of $R^5$, $R^6$ or $R^7$; then $R^1$ is not hydrogen.

In one embodiment of the instant invention are the compounds wherein

Y is selected from the group consisting of —$SO_2$—, —CO—$(CH_2)_n$— and —$(CH_2)_p$—;

R is unsubstituted or substituted phenyl where said stitutents are one or more of $R^5$, $R^6$ or $R^7$;

$R^1$ is selected from the group consisting of hydrogen, cyano, phenyl, —$CONHR^2$, —$CONR^2R^2$, —$(CH_2)_m$—$OR^2$, —$(CH_2)_p$—$S(O)_r$—$R^2$, —$(CH_2)_m$—$CO_2R^2$, —$(CH_2)_m$—$N_3$, —$(CH_2)_m$—$NH_2$ and —$(CH_2)_m$—$NR^2R^2$;

$R^5$ and $R^6$ are each independently selected from the group consisting of hydrogen, $C_{1-5}$ alkyl, $C_{1-5}$ alkoxy, halogen, —$(CH_2)_n$—CO—$R^{10}$, —$O(CH_2)_n$—CO—$R^{10}$, —$(CH_2)_n$—$R^{10}$, —$OCH_2(CH_2)_q$—$R^{10}$, —$OCH_2(CH_2)_q$—$N(R^2)$—$R^{17}$ and —$(CH_2)_n$—$N(R^2)$—$R^{17}$;

$R^7$ is selected from the group consisting of hydrogen, $R^9$ is hydrogen;

$R^{14}$ is selected from the group consisting of $C_{1-5}$ alkyl, $C_{1-5}$ alkoxy and halogen; and $R^{15}$ is selected from the group consisting of hydrogen and $C_{1-5}$ alkyl.

In one class of this embodiment are the compounds wherein

X is

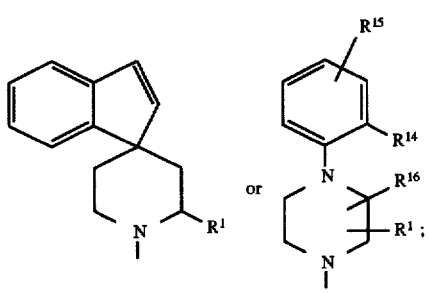

Y is selected from the group consisting of —(CH$_2$)$_p$— and —CO—(CH$_2$)$_n$—;

R$^2$ is selected from the group consisting of hydrogen, C$_{3-8}$ cycloalkyl and C$_{1-5}$ alkyl;

R$^5$ and R$^6$ are each independently selected from the group consisting of hydrogen, C$_{1-5}$ alkoxy, halogen and —(CH$_2$)$_n$—N(R$^2$)—R$^{17}$;

R$^7$ is selected from the group consisting of hydrogen and

R$^{11}$ is selected from the group consisting of hydrogen, C$_{1-5}$ alkylcarbonyl, —Z—R$^{13}$,

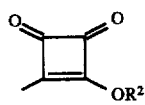

and substituted C$_{1-5}$ alkyl wherein said substituent on said alkyl is unsubstituted, mono-, di- or tri-substituted pyridyl wherein said substituents on said pyridyl are independently selected from the group consisting of halogen, C$_{1-5}$ alkyl and C$_{1-5}$ alkoxyl;

R$^{13}$ is selected from the group consisting of unsubstituted C$_{1-10}$ alkyl and substituted C$_{1-10}$ alkyl wherein said substituent is selected from the group consisting of —N(R$^2$)$_2$, —NHR$^2$ and imidazolyl;

R$^{17}$ is —Z—R$^{18}$; and

Het is selected from the group consisting of imidazolyl, benzimidazolyl, carboxymethyl-substituted benzimidazolyl and indolyl.

In one subclass are the compounds wherein X is

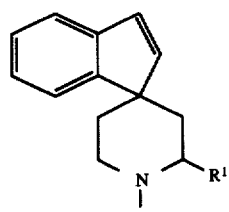

R$^1$ is selected from the group consisting of hydrogen, phenyl, cyano and —CONHR$^2$;

R$^5$ is —NH—CO—R$^{18}$;

R$^6$ and R$^7$ are hydrogen; and

R$^{18}$ is selected from Het or substituted C$_{2-5}$ alkenyl wherein said substituent is Het.

In a second subclass are the compounds wherein X is

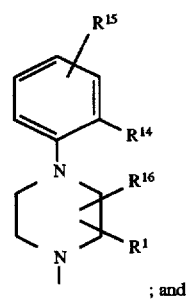

; and

R$^1$ is selected from the group consisting of hydrogen, —CONHR$^2$, —(CH$_2$)$_m$—CO$_2$R$^2$, —(CH$_2$)$_m$—OR$^2$, —(CH$_2$)$_p$—S(O)$_r$R$^2$, —(CH$_2$)$_m$—N$_3$, —(CH$_2$)$_m$—NH$_2$ and —(CH$_2$)$_m$—NR$^2$R$^2$.

Illustrative of this second subclass are the compounds of the structure

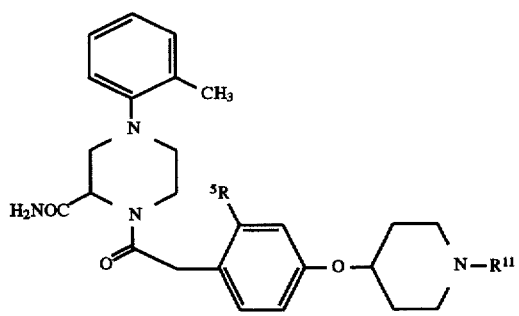

wherein R$^5$ is C$_{1-5}$ alkoxy.

Further illustrating this subclass are the compounds of the structure

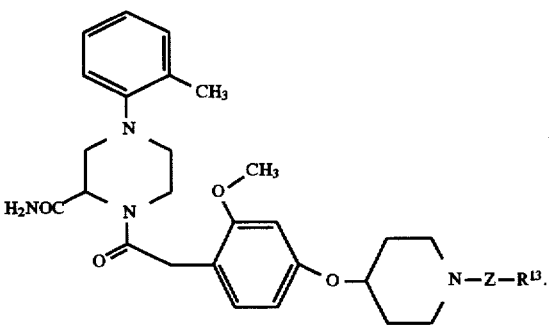

Exemplifying this subclass is the compound of the structure

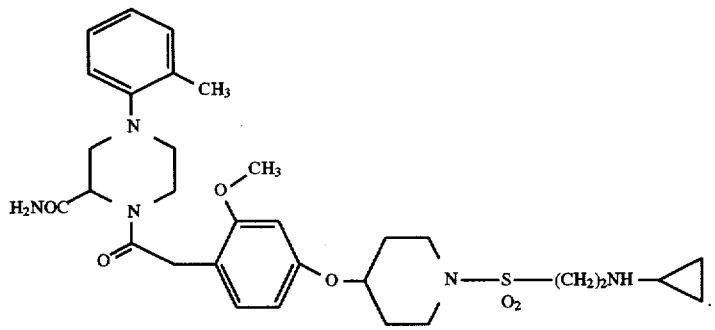

An example of this subclass is the compound of the structure

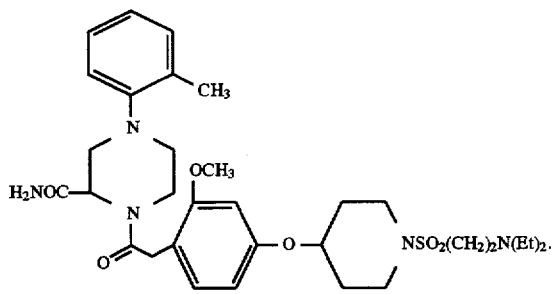

Further illustrating the instant invention is a pharmaceutical composition comprising a pharmaceutically acceptable carrier and a pharmacologically effective amount of a compound of the instant invention to prevent preterm labor in a mammal in need thereof.

Another illustration of the invention is a method of eliciting an oxytocin antagonizing effect in a mammal, comprising the step of administering to the mammal a pharmacologically effective amount of a compound of the instant invention.

Specific illustrations of the instant invention are methods of treating preterm labor, stopping labor preparatory to cesarian delivery and treating dysmenorrhea in a mammal in need thereof, comprising the step of administering to the mammal a pharmacologically effective amount of a compound of the instant invention.

Further exemplifying the invention is a method of antagonizing vasopressin from binding to its receptor site in a mammal, comprising the step of administering to said mammal a pharmacologically effective amount of a compound of the instant invention.

Specific examples of the instant invention are methods of inducing vasodilation, treating hypertension, inducing diuresis and inhibiting platelet agglutination in a mammal in need thereof, comprising the step of administering to said mammal a pharmacologically effective amount of a compound of the instant invention.

Another example of the instant invention is a method of causing contraception in a mammal in need thereof, comprising the step of administering to said mammal a pharmacologically effective amount of a compound of the instant invention.

More particularly illustrating the invention are methods of increasing fertility and embryonic survival in a farm animal and controlling the timing of estrus in a farm animal, comprising administering to the farm animal a pharmacologically effective amount of any of the compounds of the present invention. An additional illustration of the present invention is a method for improving survival of a farm animal neonate comprising controlling timing of parturition to effect delivery of the neonate during daylight hours by administering to a farm animal which is expected to deliver the neonate within 24 hours a pharmacologically effective amount of any of the compounds of the present invention.

More particularly exemplifying the invention is a compound of the formula

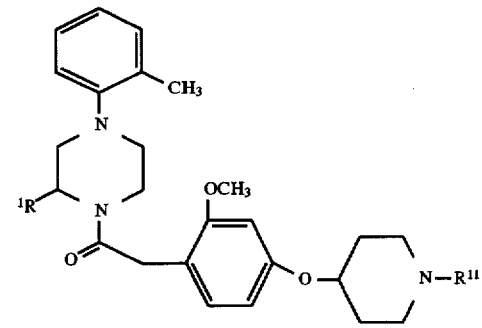

wherein $R^1$ is selected from —$CONH_2$ and

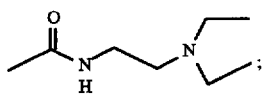

and $R^{11}$ is selected from $C_{1-5}$ alkylcarbonyl, $C_{1-5}$ alkoxycarbonyl,

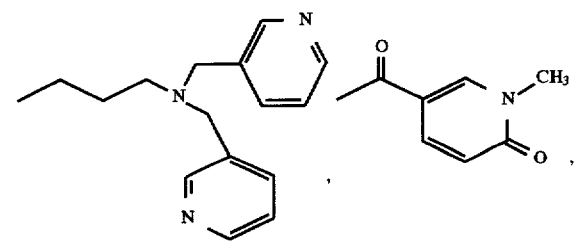

-continued
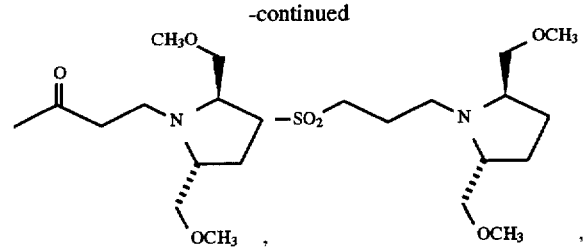
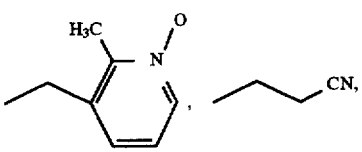
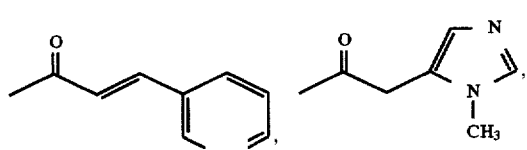
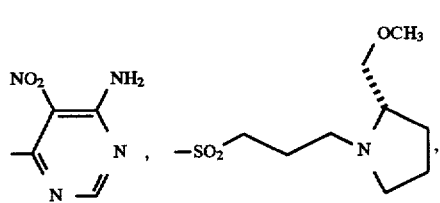
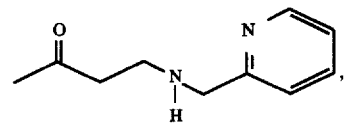
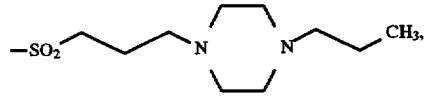
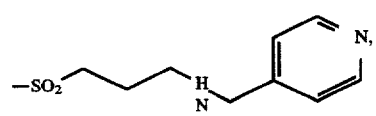
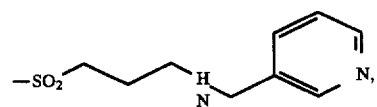
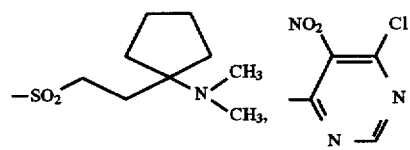
or
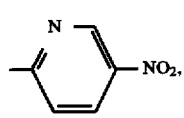
and the pharmaceutically acceptable salts thereof.
Preferably, $R^1$ is —$CONH_2$; and $R^{11}$ is selected from
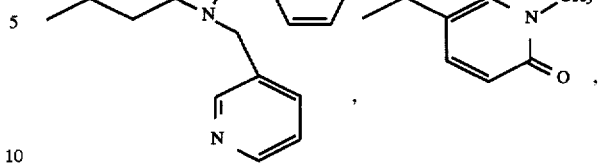
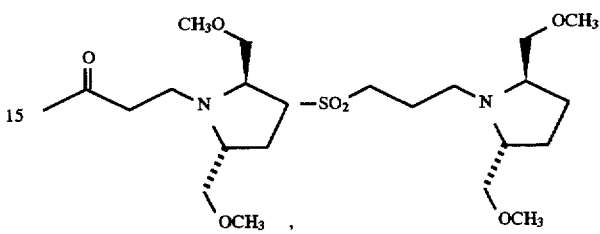
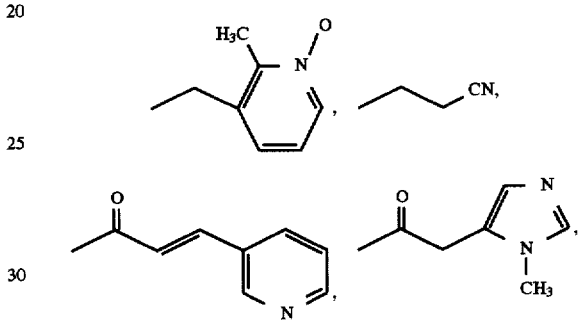
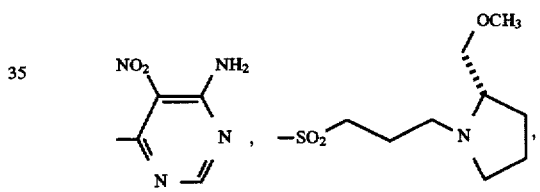
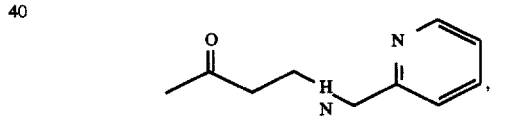
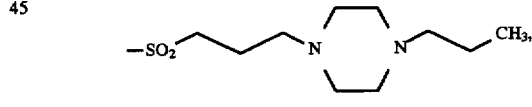
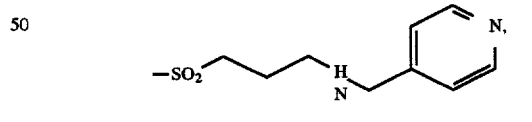
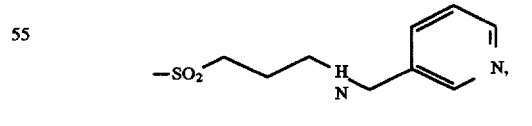
or
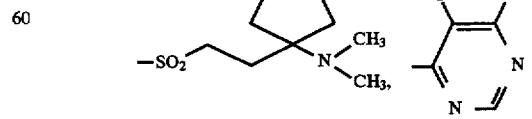

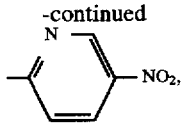

Additional examples of the invention are the use of any of the compounds described above in the preparation of a medicament for the treatment of: preterm labor, dysmenorrhea and stopping labor prior to cesarean delivery.

Salts encompassed within the term "pharmaceutically acceptable salts and esters" refer to non-toxic salts of the compounds of this invention which are generally prepared by reacting the free base with a suitable organic or inorganic acid. Representative salts include the following:

Acetate, Benzenesulfonate, Benzoate, Bicarbonate, Bisulfate, Bitartrate, Borate, Bromide, Calcium, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Sulfate, Subacetate, Succinate, Tannate, Tartrate, Teoclate ,Tosylate, Triethiodide and Valerate.

Esters encompassed within the term "pharmaceutically acceptable salts and esters" refer to non-toxic esters, preferably the alkyl esters such as methyl, ethyl, propyl, isopropyl, butyl, isobutyl or pentyl esters, of which the methyl ester is preferred. However, other esters such as phenyl—$C_{1-5}$ alkyl may be employed if desired.

Where the compounds of the instant invention contain a carboxylic acid moiety, esters, preferably alkyl esters, of the carboxylic acids may be obtained by contacting the carboxylic acid with an appropriate alcohol, preferably in the presence of an acid catalyst, for example, a mineral acid (such as hydrochloric acid or sulfuric acid), a Lewis acid (e.g., boron trifluoride) or an acidic ion exchange resin. The solvent employed for this reaction is not critical, provided that it does not adversely affect the reaction; suitable solvents include the alcohol itself, benzene, chloroform, ether and the like. Alternatively, esters may be obtained by contacting the carboxylic acid with a diazoalkane, in which the alkane moiety may be substituted or unsubstituted. This reaction is usually effected by contacting the acid with an ethereal solution of the diazoalkane. As a further alternative, the ester may be obtained by contacting a metal salt of the carboxylic acid with a halide, preferably an alkyl halide, in a suitable solvent; preferred solvents include dimethylformamide, tetrahydrofuran, dimethylsulfoxide and acetone.

Also included within the scope of the invention are polymorphs and hydrates of the compounds of the instant invention. In addition, where a compound is chiral, the separate enantiomers, substantially free of the other, are also included within the scope of the invention; further included are all mixtures of the two enantiomers.

The term "pharmacologically effective amount" shall mean that amount of a drug or pharmaceutical agent that will elicit the biological or medical response of a tissue, system, animal or human that is being sought by a researcher or clinician.

The term "alkyl" shall mean straight or branched chain alkanes of one to ten total carbon atoms, or any number within this range (i.e., methyl, ethyl, 1-propyl, 2-propyl, n-butyl, t-butyl, etc.).

The term "alkenyl" shall mean straight or branched chain alkenes with one or more degrees of unsaturation at any position on the chain, of two to ten total carbon atoms, or any number within this range.

The term "alkynyl" shall mean straight or branched chain alkynes with one or more degrees of unsaturation at any position on the chain, of two to ten total carbon atoms, or any number within this range.

The term "aryl" shall mean phenyl, napthyl or fluorenyl.

The term "cycloalkyl" shall mean cyclic rings of alkanes of three to eight total carbon atoms (i.e., cyclopropyl, cyclobutyl, cyclopentyl, cyclohexyl, cycloheptyl or cyclooctyl).

Whenever the term "alkyl" or "aryl" or either of their prefix roots appear in a name of a substituent (e.g., aralkoxyaryloxy) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The term "halogen" shall include iodine, bromine, chlorine and fluorine.

The term "preterm labor" shall mean expulsion from the uterus of a viable infant before the normal end of gestation, or more particularly, onset of labor with effacement and dilation of the cervix before the 37th week of gestation. It may or may not be associated with vaginal bleeding or rupture of the membranes.

The term "dysmenorrhea" shall mean painful menstruation.

The term "Caesarean delivery" shall mean incision through the abdominal and uterine walls for delivery of a fetus.

The term "substituted" shall be deemed to include multiple degrees of substitution by a named substitutent.

Where multiple substituent moieties are disclosed or claimed, the substituted compound can be independently substituted by one or more of the disclosed or claimed substituent moieties, singly or plurally.

The ability of the compounds of the present invention to antagonize oxytocin makes these compounds useful as pharmacologic agents for mammals, especially for humans, for the treatment and prevention of disorders wherein oxytocin may be involved. Examples of such disorders include preterm labor and especially dysmenorrhea. These compounds may also find usefulness for stoppage of labor preparatory to Cesarean delivery.

The present invention is also directed to combinations of the compounds of the present invention with one or more agents useful in the treatment of oxytocin related disorders such as preterm labor, dysmenorrhea and stopping labor prior to cesarean delivery. For example, the compounds of the instant invention may be effectively administered in combination with effective amounts of other agents used in the treatment of preterm labor, such as antenatal steroids (e.g., dexamethasone). Preferred combinations are simultaneous or alternating treatments of an oxytocin receptor antagonist of the present invention and an antenatal steroid. These combinations have beneficial effects on the neonate by both decreasing uterine activity to prolong gestation and increasing fetal maturation. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating oxytocin related conditions includes in principle any combination with any pharmaceutical composition useful for treating preterm labor, dysmenorrhea or stopping labor prior to cesarean delivery.

The oxytocin antagonist compounds of the present invention are also useful for improving reproductive efficiency in farm animals. In certain farm animals (e.g., sheep, cattle, swine and goats), the beginning of the estrous cycle is typically marked by behavioral estrus when the female animal accepts the male for mating. Ovulation of the ovarian follicle occurs shortly after onset of estrus and cells in the follicle give rise to the corpus luteum. The cells that form the corpus luteum produce progesterone and they also produce oxytocin. The secretion of oxytocin from the corpus luteum and/or pituitary acts on the uterine endometrium to stimulate the secretion of prostaglandins (in particular PGF) which, in turn, causes the regression of the corpus luteum of the ovary. PGF is, therefore, the luteolytic hormone. In the cycling animal (i.e., where mating and fertilization have not occurred), destruction of the corpus luteum removes the source of progesterone which is key to the preparation of the uterus for pregnancy. The presence of a viable conceptus (i.e., the embryo and its associated membranes) is necessary to prevent the luteolytic process. In fact, the first key signal that the conceptus must produce is the one to prevent regression of the corpus luteum (i.e., the maternal recognition of pregnancy signal). Thus, in the animal where mating and fertilization have occurred, the conceptus secretes a factor that antagonizes the action of oxytocin to induce luteolysis. This results in maintenance of a functioning corpus luteum and the continued secretion of progesterone which is obligatory to the initiation of pregnancy.

Administration of an oxytocin antagonist of the present invention at this critical period after fertilization (i.e., just prior to or during the period of maternal recognition of pregnancy) supplements the natural signal from the conceptus (i.e., maternal recognition of pregnancy) to prolong corpus luteal function. The result is to increase pregnancy rates by enhancing the chances of impregnation through a reduction in embryonic loss. Thus, to improve fertility in a farm animal, a mated animal, for example, a mated ewe, is treated with an oxytocin antagonist compound beginning on between day 10 to day 15 after onset of estrus. The oxytocin antagonist compound is administered to the mated animal for a period of one day to three weeks, preferably one week to three weeks, most preferably one week to two weeks.

The compounds of the present invention are also useful for controlling the timing of parturition in farm animals so that delivery of the neonates occurs during the daytime. Approximately 80% of livestock are delivered at night and up to 5 to 10% of newborns die because the deliveries are not monitored properly. An oxytocin antagonist compound of the present invention administered to the mother on the evening before expected delivery delays parturition so that the delivery occurs during the daylight hours. By delaying the timing of parturition, proper monitoring of the delivery and the neonates is ensured, resulting in increased survival rates of the newborns.

In addition, the oxytocin antagonists of the instant invention can also be used to control the timing of estrus in a cycling farm animal by preventing luteal regression. An oxytocin antagonist compound of the instant invention is administered to a cycling farm animal prior to expected estrus to prevent regression of the corpus luteum. Daily administration of the compound retards estrus until administration of the compound ceases. Preferably, the oxytocin antagonist compound is administered at least 1 day prior to expected estrus. By delaying estrus in a group of farm animals, a farmer can synchronize estrus among the group to provide time and cost savings in farm management.

The compounds of the present invention also bind to the vasopressin receptor and are therefore useful as vasopressin antagonists. Vasopressin antagonists are useful in the treatment or prevention of disease states involving vasopressin disorders, including their use as diuretics and their use in congestive heart failure.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a tocolytic agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.3–6.0 gm/day orally. More particularly, when administered orally for the treatment of preterm labor, an effective daily dose will be in the range of 0.05 mg/kg to about 100 mg/kg of body weight, preferably, from 0.5 mg/kg to 50 mg/kg, administered in single or divided dose. Intravenously, the most preferred doses will range from 0.1 to about 10 mg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethyl-aspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Abbreviations used in the Examples are as follows:
BOP=benzotriazol-1-yloxytris(dimethylamino) phosphonium hexafluorophosphate
DIEA=diisopropylethylamine
DMF=dimethylformamide
EtOAc=ethyl acetate
EtOH=ethanol
EDC=1-ethyl-3-(3-dimethylaminopropyl)carbodiimide
FAB MS=fast atom bombardment mass spectroscopy
HOBT or HBT=1-hydroxybenzotriazole
HPLC=high pressure liquid chromatography
MeOH=methanol
NMR=nuclear magnetic resonance
THF=tetrahydrofuran
TLC=thin layer chromatography All solvents were reagent grade and stored over 4 Å molecular sieves. THF was distilled from calcium hydride under inert atmosphere. Dioxane was dried and freed of peroxides by passage through a column of activity I neutral alumina.

Determination of reaction pH was estimated by spotting an aliquot from the reaction mixture on wetted E. Merck pH sticks. $^1$H NMR spectra were measured at 300 MHz on a Varian XL-300, at 400 MHz on a Varian XL-400, and at 360 MHz on a Nicolet NT-360 using $(CH_3)_4Si$ as an internal standard. Fast atom bombardment mass spectra (FAB MS) were obtained on a VG-ZAB-HF spectrometer.

Analytical HPLC were run on a Spectra Physics SP4270/8800 instrument using the following conditions:

Column: Vydac $C_{18}$, 0.21×15 cm
Mobile Phases
A=0.1% by volume TFA in $H_2O$; B=MeOH;
C=0.1 % by volume TFA in acetonitrile
Gradient
T=0 min, 95% A, 5% C
T=15 min, 5% A, 95% C
Flow=1.5 mL/min
UV detection at 214 nm Pressurized silica gel column chromatography using 230–400 mesh silica gel was performed according to the method of Still, Kahn, and Mitra (J. Org. Chem. (1978) vol. 43, p.2923).

The compounds of the present invention can be prepared readily according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail.

The most preferred compounds of the invention are any or all of those specifically set forth in these Examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

The compounds and pharmaceutically acceptable salts of the present invention can be synthesized according to the general methods outlined in Schemes 1–3. The spiroindene compounds of the instant invention can be prepared as shown in Scheme 1. Accordingly, spiro[1H]indene-1,4'-piperidine I (prepared as described in U.S. Pat. No. 4,894, 396) is dissolved in an aprotic organic solvent, preferably methylene chloride or N,N-dimethylformamide (DMF) following the usual techniques for the exclusion of moisture. To this solution is then added an acylating agent, such as a carboxylic acid chloride, carboxylic acid anhydride or sulfonic acid chloride, or the like; preferably, a phenylacetic acid analog is added, followed by an amide bond forming agent, for example 1-ethyl-3-(3-dimethylamino-propyl)-carbodiimide hydrochloride (EDC), and an activating agent like 1-hydroxybenzotriazole (HBT). The reaction mixture temperature is maintained between 0° C. and 27° C., preferably 23° C., and the pH is monitored throughout the course of the reaction and is adjusted when necessary to approximately 8 with a base like triethylamine (TEA). Extractive workup and purification according to standard procedures affords II.

Spiro[1H]indene-1,4'-piperidine I can also be derivatized in the 2'-position by first forming an intermediate chloramine with a halogenating agent, preferably tert-butylhypochlorite, followed by elimination of the halide with potassium superoxide in ethyl ether to give III. Imine III is then trapped with a suitable alkylmetal or phenylmetal reagent, for example n-butyllithium or phenyllithium, to give derivatives like IV. Alternatively, functional groups like a nitrile can be introduced with the aid of an agent like trimethylsilylcyanide to give an aminonitrile which is then further transformed to an amide like VI according to standard methodology. Both IV and VI can then be converted to V and VII, respectively, employing the acylating methodology described above.

SCHEME I
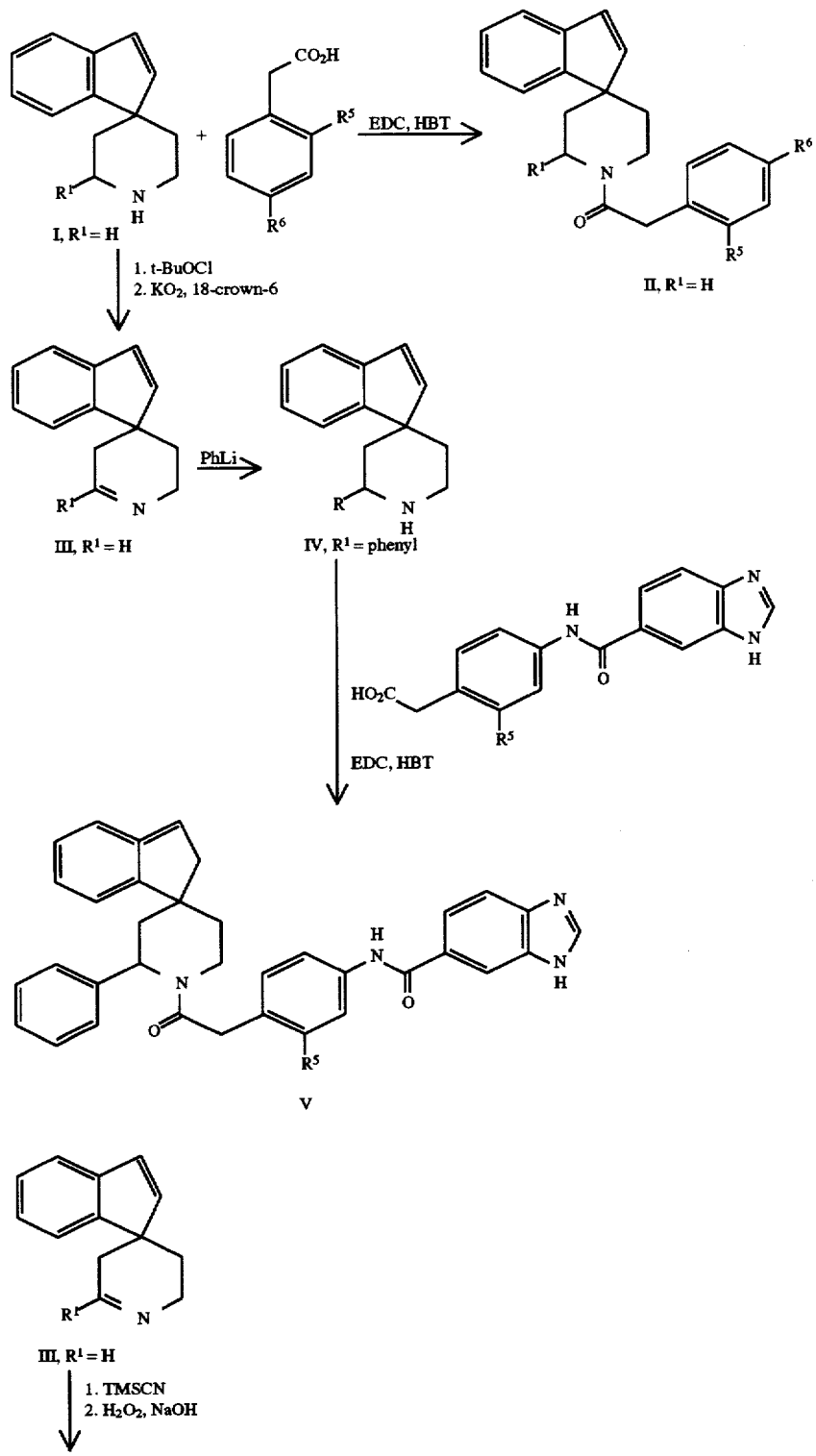

-continued
SCHEME 1

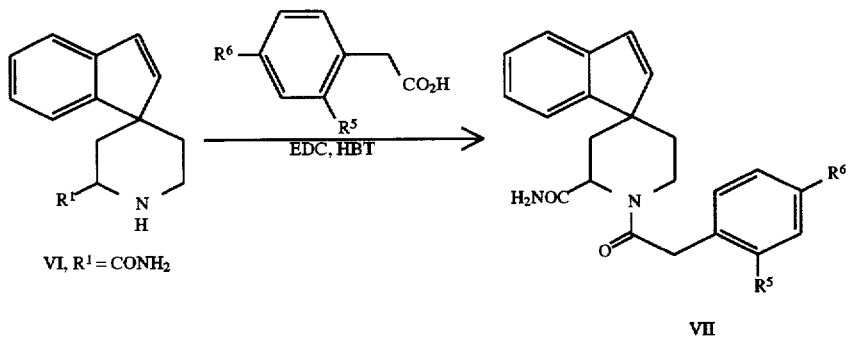

VI, R¹ = CONH₂

VII

The compounds of the present invention are also prepared as outlined in Scheme 2, wherein 1-(2-tolyl)piperazine VIII is acylated with a carboxylic acid derivative, preferably a phenylacetic acid analog, according to common amide bond forming techniques. A preferred method consists of adding the water soluble reagent (EDC) and an activating agent like (HBT) to a solution of DMF, at ambient temperature, containing 1-(2-tolyl)piperazine and a phenylacetic acid analog. The reaction mixture temperature is maintained at 23° C., and the pH is monitored throughout the course of the reaction and is adjusted when necessary to approximately 8 with a trialkylamine base like (TEA) or diisopropylethylamine (DIEA). Extractive workup and standard purification yields the product IX.

SCHEME 2

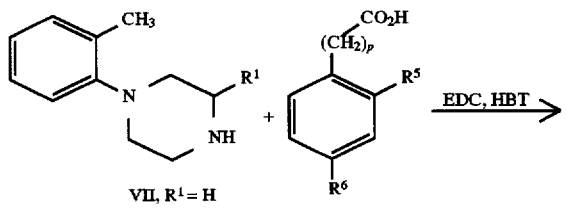

VII, R¹ = H

-continued
SCHEME 2

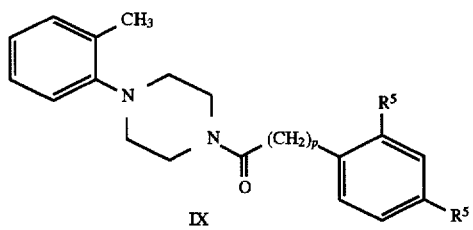

IX

A further method for preparing the compounds of the present invention is shown in Scheme 3 and consists of reacting 4-(2-methylphenyl)piperazine-2-carboxamide X (prepared either according to the procedure in *J. Med. Chem.* 1992, 35, 743–750 or in *Tetrahedron Letters*, 1988, 29(52), 6913–6916) with a carboxylic acid derivative, preferably a phenylacetic acid analog, according to common amide bond forming techniques to give XI and XII. The latter compound is then further elaborated at the piperidinol nitrogen by acylation, for example with 3,4-diethoxy-3-cyclobutene-1, 2-dione to afford XIII or with imidazole acetic acid to yield XV. The piperidinol nitrogen atom can also be alkylated with a suitable alkylating agent, for example picolyl chloride, in an appropriate solvent like DMF, in the presence of an inorganic base or preferably a trialkylamine base like TEA or DIEA to afford XIV. The terminal piperidinol nitrogen atom in XII can also be sulfonylated with a sulfonyl chloride derivative, for example with chloroethylsulfonyl chloride, in an organic solvent, preferably ethyl acetate or methylene chloride using a base, preferably DIEA. The resulting sulfonamide derivative is then converted to the desired product XVI using standard synthetic methodology.

SCHEME 3

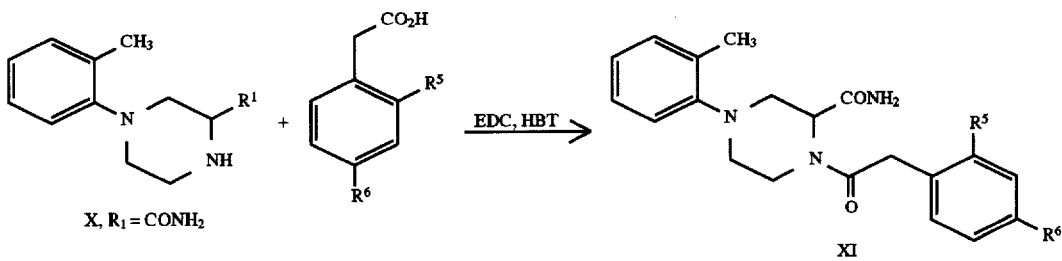

X, R₁ = CONH₂

XI

-continued
SCHEME 3
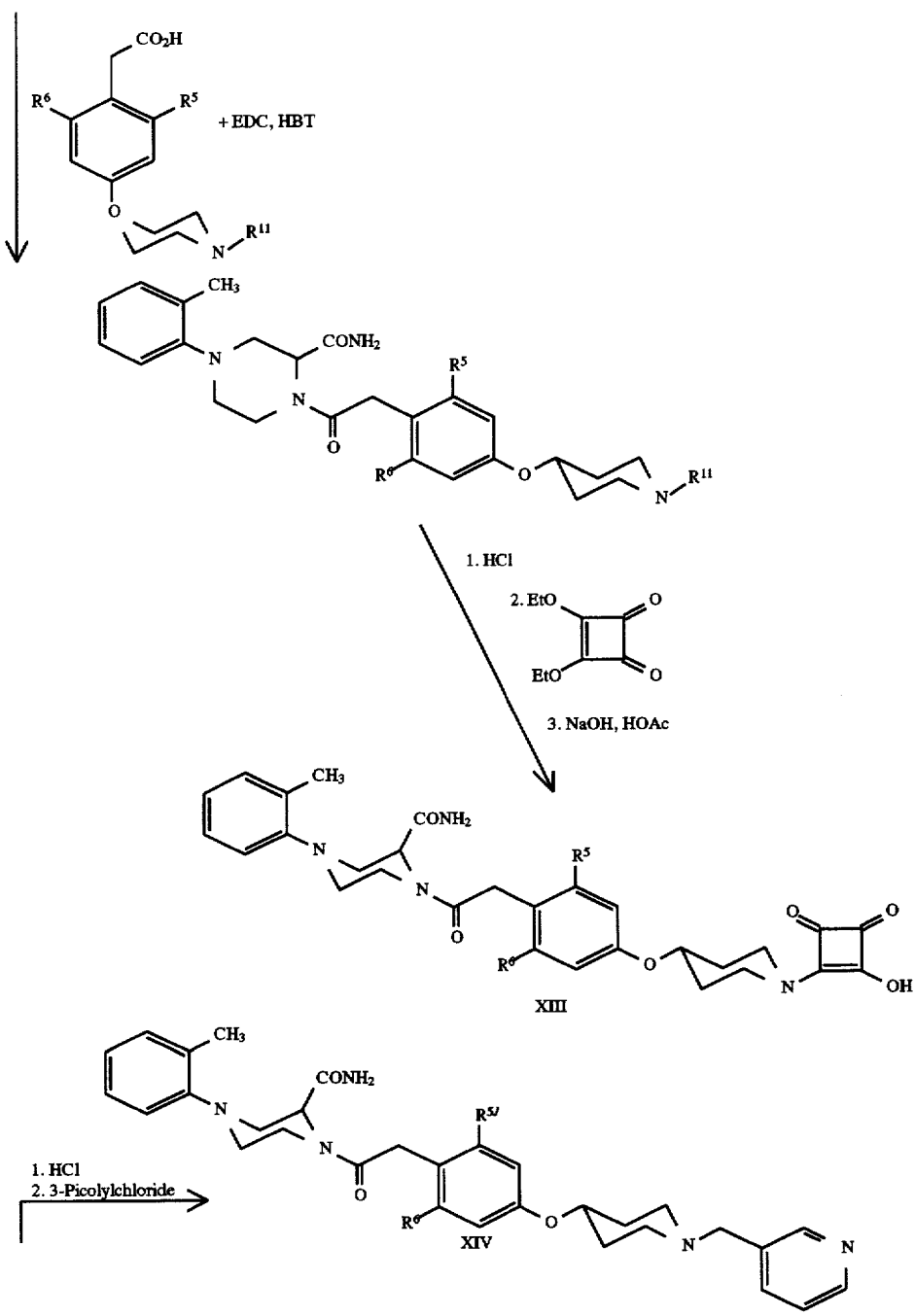

-continued
SCHEME 3

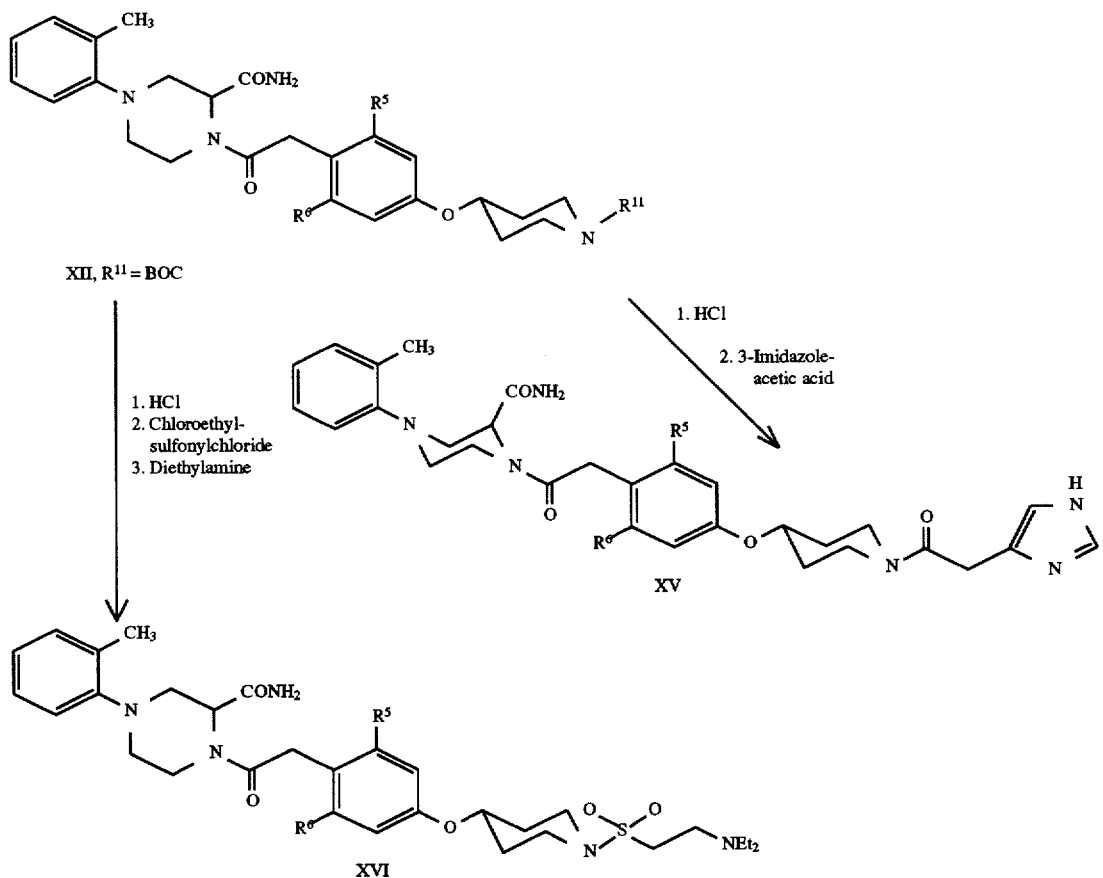

EXAMPLE 1

1'-(2,4-Dimethoxyphenylacetyl)-spiro[1H]indene-1,4'-piperidine

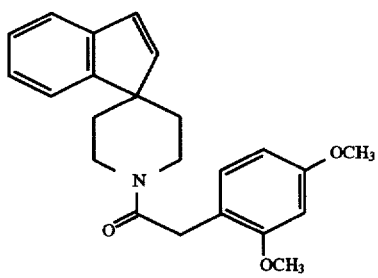

Spiro[1H]indene-1,4'-piperidine hydrochloride (100 mg, 0.45 mmol) was dissolved in DMF (2 ml) and treated with 2,4-dimethoxy-phenylacetic acid (97.3 mg, 0.5 mmol), EDC (95 mg, 0.5 mmol), and HBT (67 mg, 0.5 mmol). The pH of the mixture was adjusted to ca. 9.5 (moistened E. Merck colorpHast indicator) with triethylamine, and the mixture was stirred at ambient temperature for 18 hours. The solvent was removed in vacuo and the residue was treated with water and extracted with ethyl acetate. The combined ethyl acetate layers were washed with brine, dried over sodium sulfate, filtered, and evaporated to dryness in vacuo. The residue was chromatographed on silica gel eluted with 8% ether in methylene chloride. The combined product fractions were evaporated to dryness in vacuo and the residue crystallized from ether to give 1'-(2,4-dimethoxyphenylacetyl)-spiro[1H]indene-1,4'-piperidine: mp 93°–108° C.

$^1$H-NMR: Consistent with structure

TLC: silica gel, 10% ether in methylene chloride: single component, $R_f$=0.41

FABMS: M+H @ m/e=364

HPLC: 98%

Anal. cal'd for $C_{23}H_{25}NO_3 \cdot 0.55 H_2O$: C, 73.98; H, 7.05, N, 3.75. Found: C, 73.70; H, 7.30; N, 4.04.

EXAMPLE 2

1'-(4-(Benzimidazole-5-carboxylamino)phenylacetyl)-2'-phenylspiro[1H]indene-1,4'-piperidine

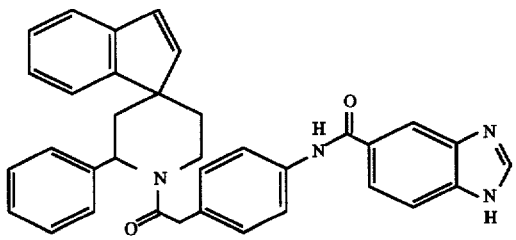

3',4',5',6'-Tetrahydrospiro[1H]indene-1,4'-pyridine

Spiro[1H]indene-1,4'-piperidine hydrochloride (5 g, 22.6 mmol) was partitioned between saturated aqueous sodium bicarbonate and ether. The aqueous layer was extracted with ether. The combined ether layers were dried over sodium sulfate, filtered, and concentrated in vacuo to 50 ml. The solution of spiro[1H]indene-1,4'-piperidine was cooled in ice and treated with t-butyl hypochlorite (3.37 ml, 3.06 g, 28.2 mmol). The mixture was stirred in the cold for 30 min. An additional 1.0 ml of t-butyl hypochlorite was added and the mixture stirred another 15 min. A final 0.5 ml portion of t-butyl hypochlorite was added and the mixture stirred an additional 15 min. The ether layer was washed with water, with dilute sulfuric acid, with water, and with brine, dried over magnesium sulfate, filtered, and concentrated in vacuo to 10 ml. The solution was re-dried over magnesium sulfate and calcium carbonate for 1 hour, then filtered directly into an ether suspension of potassium superoxide (3.53 g, 49.7 mmol) and 18-crown-6 (100 mg). The mixture was stirred 4.5 hours at ambient temperature, then filtered and diluted with ether to 75 ml to provide a solution of 3',4',5',6'-tetrahydrospiro[1H]indene-1,4'-pyridine of nominal 0.3M concentration.

2'-Phenyl-spiro[1H]indene-1 4'-piperidine

3',4',5',6'-Tetrahydrospiro[1H]indene-1,4'-pyridine (15 ml of 0.3M ether solution; 4.5 mmol) was added to phenyllithium solution (5.27 ml of 1.8M solution in 70/30 cyclohexane/ether, 9.5 mmol) stirred in an ice bath. The mixture was stirred 30 min. in the cold, then 18 hours at ambient temperature. Water was added, and the mixture extracted with ether. The combined ether layers were washed with water, then with brine, dried over sodium sulfate, filtered, and evaporated to dryness in vacuo. The residue was chromatographed on silica gel eluted with 90:7:0.7:0.7 methylene chloride:methanol:water:acetic acid. The combined product fractions were evaporated to dryness, and the residue was rechromatographed on silica gel eluted with 80:4:0.4 methylene chloride:methanol:concentrated ammonia. The product fractions were evaporated to dryness in vacuo to give 2'-phenyl-spiro[1H]Indene- 1,4'-piperidine.

4-(Benzimidazole-5-carboxylamino)phenylacetic acid

Methyl 4-aminophenylacetate hydrochloride (6.9 g, 34 mmol), benzimidazole-5-carboxylic acid (5.0 g, 31 mmol), EDC (9.0 g, 47 mmol) and HBT (6.4 g , 47 mmol) were combined in DMF (250 ml). The pH of the mixture was adjusted to ca. 9 with diisopropylethylamine, and the mixture was stirred at ambient temperature for 3 days. The solvent was removed in vacuo, and the residue was treated with aqueous sodium bicarbonate and extracted with ethyl acetate. The combined ethyl acetate layers were washed with water and with brine, dried over sodium sulfate, filtered, and evaporated to dryness in vacuo to give methyl 4-(benzimidazole-5-carboxylamino)phenylacetate.

Methyl 4-(benzimidazole-5-carboxylamino) phenylacetate (3.6 g, 12 mmol) was dissolved in methanol (50 ml) and treated with aqueous sodium hydroxide (4.8 g, 120 mmol, in 50 ml of water) and stirred at ambient temperature for 2 hours. The mixture was concentrated in vacuo and the residue acidified with concentrated HCl. The mixture was filtered to give 4-(benzimidazole-5-carboxylamino)phenylacetic acid.

1'-(4-(Benzimidazole-5-carboxylamino) phenylacetyl)-2'-phenylspiro[1H]indene-1 4'-piperidine 2'-Phenyl-spiro[1H]indene-1,4'-piperidine (55 mg, 0.21 mmol) was dissolved in DMF (1 ml) and treated with 4-(benzimidazole-5-carboxylamino)phenylacetic acid (93.2 mg, 0.316 mmol), EDC (605 mg, 0.316 mmol) and HBT (42.7 mg, 0.316 mmol). The pH of the mixture was adjusted to ca. 9.5 (moistened E. Merck colorpHast indicator) with triethylamine, and the mixture was stirred at ambient temperature for 18 hours. The solvent was removed in vacuo and the residue treated with aqueous sodium bicarbonate and extracted with ethyl acetate. The combined ethyl acetate layers were washed with brine, dried over sodium sulfate, filtered, and evaporated to dryness in vacuo. The residue was chromatographed on silica gel eluted with 115:10:1 methylene chloride:methanol:concentrated ammonia. The combined product fractions were evaporated to dryness in vacuo and the residue triturated with ether to give 1'-(4-(benzimidazole-5-carboxylamino)phenylacetyl)-2'-phenyl-spiro[1H]indene-1,4'-piperidine: mp 175°–188° C.

¹H-NMR: Consistent with structure

TLC: silica gel, 115: 10:1 methylene chloride:methanol :concentrated ammonia: single component, $R_f$=0.30

FABMS: M+H @ m/e=539

HPLC: 95%

Anal. cald for $C_{35}H_{30}N_4O_2.0.1C_4H_{10}O .0.3CH_2Cl_2.0.2 H_2O$: C, 74.55 H, 5.61 N, 9.74. Found: C, 74.26; H, 5.74; N, 9.48.

EXAMPLE 3

1'-(4-(Benzimidazole-5-carboxylamino)phenylacetyl)-spiro[1H]indene-1,4'-piperidine-2'-carboxamide diastereomer A and diastereomer B

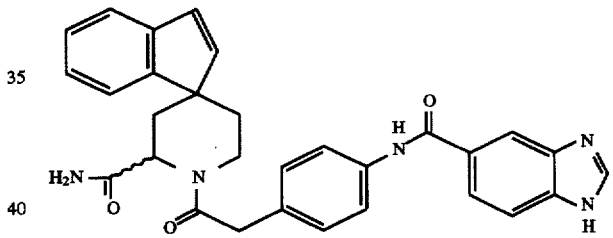

2'-Cyano-spiro[1H]indene-1,4'-piperidine

3',4',5',6'-Tetrahydrospiro[1H]indene-1,4'-pyridine (21 ml of 0.22M ether solution; 4.6 mmol) was added slowly to a solution of trimethylsilylcyanide (1.32 ml, 0.984 g, 9.92 mmol) stirred in ether in an ice bath. The mixture was stirred in the cold for 30 min, then at ambient temperature for 18 hours. The solution was washed with water and with brine, dried over sodium sulfate, filtered, and evaporated to dryness in vacuo. The residue was chromatographed on silica gel eluted with 20% ether in methylene chloride. The combined product fractions were evaporated to dryness in vacuo and the residue was crystallized from ether/hexane to give 2'-cyano-spiro[1H]indene-1,4'-piperidine.

Spiro[1H]indene-1 4'-piperidine-2'-carboxamide

2'-Cyano-spiro[1H]indene-1,4'-piperidine (2.0 g, 9.5 mmol) was dissolved in 95% ethanol (21 ml) and treated with 10% aqueous sodium hydroxide (1 ml, 2.5 mmol) followed by 30% aqueous hydrogen peroxide (1.08 ml, 9.5 mmol). The mixture was stirred in an ice bath for 10 min, at ambient temperature for 30 min, then at 50° C. (oil bath) for 2.5 hours. The mixture was poured into water (200 ml) and extracted with methylene chloride. The combined organic layers were washed with 10% aqueous sodium bisulfite, dried over sodium sulfate, filtered, and evaporated to dryness in vacuo. The residue was chromatographed on silica gel eluted with 90:20:2:2 methylene chloride:methanol:water:acetic acid. The separated fractions were evaporated to dryness in vacuo to give the individual diastereomers A and B of spiro[1H]indene-1,4'-piperidine-2'-carboxamide.

1'-(4-(Benzimidazole-5-carboxylamino) phenylacetyl)-spiro[1H]indene-1,4'-piperidine-2'-carboxamide diastereomer A Spiro[1H]indene-1,4'-piperidine-2'-carboxamide, diastereomer A (45 mg, 0.2 mmol), 4-(benzimidazole-5-carboxylamino)phenylacetic acid (64 mg, 0.22 mmol), EDC (41.6 mg, 0.22 mmol), and HBT (29.3 mg, 0.22 mmol) were combined in DMF (2 ml). The mixture was adjusted to pH ca. 9.5 (moistened E. Merck colorpHast indicator) with triethylamine and stirred at ambient temperature for 18 hours. The solvent was removed in vacuo and the residue was treated with water and extracted with ethyl acetate containing 10% n-butanol. The combined organic layers were washed with brine, dried over sodium sulfate, filtered, and evaporated to dryness in vacuo. The residue was chromatographed on silica gel eluted with 80:10:1 methylene chloride:methanol:concentrated ammonia. The combined product fractions were evaporated to dryness in vacuo and the residue crystallized from ether to give 1'-(4-(benzimidazole-5-carboxylamino)phenylacetyl)-spiro[1H]indene-1,4'-piperidine-2'-carboxamide, diastereomer A: mp 185°–207° C.

$^1$H-NMR: Consistent with structure

TLC: silica gel, 80:10:1 methylene chloride:methanol:concentrated ammonia: single component, $R_f$=0.30

FABMS: M+H @ m/e=506

HPLC:88%

Anal. cal'd for $C_{30}H_{27}N_5O_3 \cdot 1.3\ H_2O$: C, 68.11; H, 5.64; N, 13.24. Found: C, 67.97; H, 5.54; N, 12.95.

1'-(4-(Benzimidazole-5-carboxylamino) phenylacetyl)-spiro[1H]indene-1,4'-piperidine-2'-carboxamide, diastereomer B The procedure described for preparation of 1'-(4-(Benzimidazole-5-carboxylamino)phenylacetyl)-spiro[1H]indene-1,4'-piperidine-2'-carboxamide, diastereomer A was carried out using spiro[1H]indene-1,4'-piperidine-2'-carboxamide, diastereomer B in place of spiro[1H]indene-1,4'-piperidine-2'-carboxamide, diastereomer A. Chromatography was with 100:10:1methylene chloride:methanol: concentrated ammonia. The combined product fractions were evaporated to dryness in vacuo and the residue crystallized from ether to give 1'-(4-(benzimidazole-5-carboxylamino)phenylacetyl)spiro[1H]indene-1,4'-piperidine-2'-carboxamide, diastereomer B: mp 181°–202° C.

$^1$H-NMR: Consistent with structure

TLC: silica gel, 80:10:1 methylene chloride:methanol:concentrated ammonia: single component, $R_f$=0.25

FABMS: M+H @ m/e=506

HPLC:98%

Anal. cal'd for $C_{30}H_{27}N_5O_3 \cdot 1.3\ H_2O$: C, 68.11; H, 5.64; N, 13.24. Found: C, 68.03; H, 4.83; N, 13.07.

EXAMPLE 4

1'-(4-(Indole-6-carboxylamino)phenylacetyl)spiro [1H]indene-1,4'-piperidine

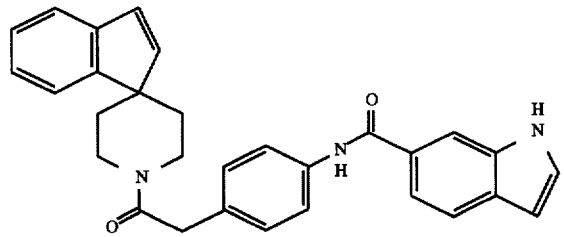

Spiro[1H]indene-1,4'-piperidine hydrochloride (2.8 g, 12.6 mmol) was dissolved in DMF (40 ml) and treated with 4-aminophenylacetic acid (2.1 g, 13.9 mmol) followed by BOP reagent (6.13 g, 13.9 mmol). Diisopropylethylamine was added to adjust the pH of the mixture to ca. 9.5 (moistened E. Merck colorpHast indicator). The mixture was stirred at ambient temperature for 1 hour, then concentrated in vacuo. The residue was treated with water and extracted with ethyl acetate. The combined organic layers were washed with water, then with brine, dried over sodium sulfate, filtered, and evaporated to dryness in vacuo. The residue was chromatographed on silica gel eluted with 65:35 ethyl acetate:methylene chloride. The product fractions were combined and evaporated to dryness to give 1'-(4-aminophenylacetyl)spiro[1H]indene-1,4'-piperidine.

1'-(4-aminophenylacetyl)spiro[1H]indene-1,4'-piperidine (104 mg, 0.33 mmol), indole-6-carboxylic acid (58 mg, 0.36 mmol; prepared as described in U.S. Pat. No. 4,894,386), EDC (68.8 mg, 0.36 mmol), and HBT (48.6 mg, 0.36 mmol) were combined in DMF (2 ml) and treated with triethylamine to bring the pH of the mixture (moistened E. Merck colorpHast indicator) to ca. 9.5. The mixture was stirred at ambient temperature for 5 days. The solvent was removed in vacuo and the residue was diluted with water and extracted with ethyl acetate. The combined organic layers were washed with brine, dried over sodium sulfate, filtered, and evaporated to dryness in vacuo. The residue was chromatographed on silica gel eluted with 266:10:1 methylene chloride:methanol:concentrated ammonia. The combined product fractions were evaporated to dryness in vacuo, and the residue was crystallized from ethyl acetate to give 1'-(4-(indole-6-carboxylamino)phenylacetyl)spiro[1H]indene-1,4'-piperidine: mp 259°–262° C.

$^1$H-NMR: Consistent with structure

TLC: silica gel, 266:10:1 methylene chloride:methanol:concentrated ammonia: single component, $R_f$=0.20

FABMS: M+H @ m/e=462 (free base)

HPLC: 95%

Anal. cal'd for $C_{30}H_{27}N_3O_2 \cdot 0.1EtOAc \cdot 0.15\ H_2O$: C, 77.18 H, 5.99 N, 8.88. Found: C, 76.89; H, 5.97; N, 8.92.

EXAMPLE 5

1-Benzyl-4-(2-methylphenyl)piperazine-2-carboxamide

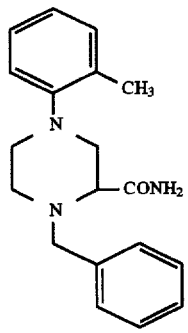

2-Benzylaminoethanol (18.8 ml, 20 g, 0.13 mol) was converted to N-(2-chloroethyl)-N-benzylamine hydrochloride with thionyl chloride (19 ml, 31 g, 0.26 mol) according to the procedure described in J. Chem. Soc. 1955, 896. N-(2-chloroethyl)-N-benzylamine hydrochloride (4.0 g, 19 mmol) was converted to N-benzyl-N'-(2-methylphenyl)-1, 2-diaminoethane hydrochloride by the procedure of Syn. Comm. 18, 45–50 (1988), using o-toluidine (6.1 ml, 6.1 g, 57 mmol) in place of aniline. 1-benzyl-4-(2-methylphenyl) piperazine-2-carboxamide was prepared from 2,3-dibromopropionamide (7.9 g, 34 mmol) by the procedure of J. Med. Chem. 35, 743–750 (1992) using N-benzyl-N'-(2-methylphenyl)-1,2-diaminoethane hydrochloride (4.95 g, 18 mmol) in place of N-benzyl-N'-phenyl-1,2-diaminoethane hydrochloride.

$^1$H-NMR: Consistent with structure

TLC: silica gel, 5% methanol in methylene chloride: single component, Rf=0.51

FABMS: M+H @ m/e=310

HPLC: 98%

Anal. cald for $C_{19}H_{23}N_3O \cdot 0.2\ H_2O$: C, 72.90; H, 7.54; N, 13.43. Found: C, 72.83; H, 7.29; N, 13.53.

EXAMPLE 6

1-(2,4-Dimethoxyphenylacetyl)-4-(2-methylphenyl) piperazine

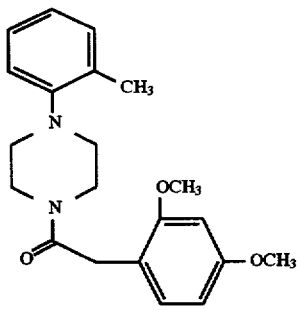

1-(2-methylphenyl)piperazine (.087 g, 0.41 mmol) and 2,4-dimethoxyphenylacetic acid (0.096 g, 0.49 mmol) were dissolved in 20 DMF (5 ml) and treated with EDC (0.091 g, 0.47 mmol) and HBT (0.071 g, 0.52 mmol). Triethylamine was added to the stirred mixture to bring the pH (moistened E. Merck colorpHast indicator) to ca. 9. The mixture was stirred at ambient temperature for 18 hours, then concentrated in vacuo. The residue was taken up in ethyl acetate, and the ethyl acetate layer was washed with saturated aqueous sodium bicarbonate and brine, dried over sodium sulfate, filtered, and the filtrate was concentrated to dryness in vacuo. The residue was chromatographed on silica gel eluted with 1.5% methanol in methylene chloride. The combined product fractions were evaporated to dryness in vacuo to give the title compound.

$^1$H-NMR: Consistent with structure

TLC: silica gel, 5% methanol in methylene chloride: single component, Rf=0.72

FABMS: M+H @ m/e=355

HPLC: 96%

Anal. cal'd for $C_{21}H_{26}N_2O_3 \cdot 0.05\ Et_2O \cdot 0.55\ H_2O$: C, 69.18; H, 7.56; N, 7.61. Found: C, 69.15; H, 7.31; N, 7.75.

EXAMPLE 7

1-(2,4-Dimethoxyphenylacetyl)-4-(2-methylphenyl) piperazine-2-carboxamide

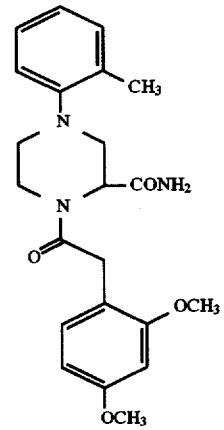

1-benzyl -4-(2-methylphenyl)piperazine-2-carboxamide (2.64 g, 8.53 mmol) and palladium hydroxide/carbon (430 mg) were combined in a mixture of methanol (35 ml) and ethanol (35 ml) and shaken in an atmosphere of hydrogen at 55 psi for 6 hours at ambient temperature. The mixture was filtered and the filtrate was concentrated in vacuo. The residue was reconcentrated in vacuo from ether three times to provide 4-(2-methylphenyl)piperazine-2-carboxamide.

4-(2-Methylphenyl)piperazine-2-carboxamide (39 mg, 0.18 mmol), 2,4-dimethoxyphenylacetic acid (42 mg, 0.21 mmol), EDC (42 mg, 0.22 mmol) and HBT (31 mg, 0.23 mmol) were combined in DMF (5 ml) and treated with triethylamine to adjust the pH to ca. 9 (moistened E. Merck colorpHast indicator). The mixture was stirred at ambient temperature for 64 hours. The solvent was removed in vacuo and the residue was chromatographed on silica gel eluted with 2% methanol in methylene chloride. The combined product fractions were evaporated to dryness in vacuo to provide the title compound.

$^1$H-NMR: Consistent with structure

TLC: silica gel, 5% methanol in methylene chloride: single component, Rf=0.45

FABMS: M+H @ m/e=398

HPLC: 99%

Anal. cal'd for $C_{22}H_{27}N_3O_4$: C, 66.48; H, 6.85; N, 10.57. Found: C, 66.54; H, 6.91; N, 10.36.

EXAMPLE 8

1-(4-(Benzimidazol-5-carboxylamino)phenylacetyl)-4-(2-methylphenyl)piperazine-2-carboxamide

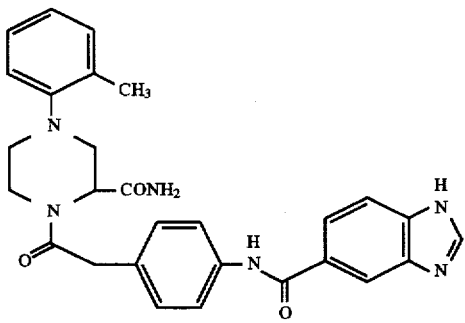

4-(2-Methylphenyl)piperazine-2-carboxamide (0.123 g, 0.56 mmol), 4-(benzimidazol-5-carboxylamino) phenylacetic acid (204 mg, 0.69 mmol), EDC (131 mg, 0.68 mmol) and HBT (96 mg, 0.71 mmol) were combined in DMF (5 ml) and treated. Triethylamine was added to the stirred mixture to bring the pH (moistened E. Merck colorpHast indicator) to ca. 9. The mixture was stirred at ambient temperature for 18 hours, then concentrated in vacuo. The residue was taken up in ethyl acetate, and the ethyl acetate layer was washed with saturated aqueous sodium bicarbonate and brine, dried over sodium sulfate, filtered, and the filtrate was concentrated to dryness in vacuo. The residue was chromatographed on silica gel eluted with 92:8:0.8 methylene chloride:methanol:concentrated ammnonia. The combined product fractions were evaporated to dryness in vacuo and the residue was reconcentrated from ether, then triturated with ether and filtered to give the title compound.

$^1$H-NMR: Consistent with structure

TLC: silica gel, 95:5:0.5 methylene chloride:methanol:concentrated ammonia: single component, $R_f$=0.29

FABMS: M+H @ m/e=497

HPLC: 97%

Anal. cal'd for $C_{28}H_{28}N_6O_3 \cdot 0.2$ $Et_2O \cdot 0.6$ $H_2O$: C, 66.24; H, 6.02; N, 16.09. Found: C, 66.26; H, 5.91; N, 15.83.

EXAMPLE 9

1-(2-Methoxy-4-(1-acetyl-4-piperidyloxy) phenylacetyl)-4-(2-methylphenyl)piperazine-2-carboxamide

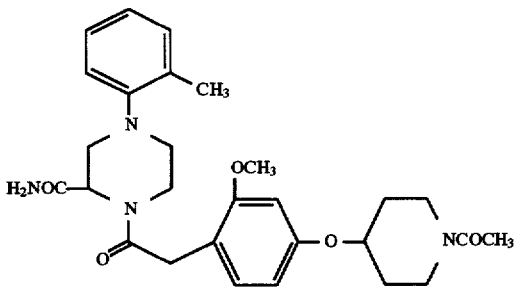

4-Hydroxypiperidine (15.52 g, 0.153 mol) in methylene chloride (100 ml) was treated with a solution of di-t-butyl dicarbonate (33.2 g, 0.152 mol) in methylene chloride (100 ml) added dropwise over 20 min. The mixture was stirred at ambient temperature for 3 hours, then evaporated to dryness in vacuo. The residue was concentrated from ether to give 1-Boc-4-hydroxypiperidine.

Methyl 2,4-dihydroxybenzoate (5.1 g, 30.33 mmol) and triphenylphosphine (9.52 g, 36.3 mmol) were stirred in THF (200 ml) under nitrogen. The mixture was cooled in an ice bath and treated with a solution of 1-Boc-4-hydroxypiperidine (6.8 g, 33.8 mmol) and diethyl azodicarboxylate (5.73 ml, 6.34 g, 36.4 mmol) in THF (100 ml) added dropwise over 30 min. The mixture was stirred at ambient temperature for 18 hours, then diluted with ethyl acetate and washed with 1M NaOH, saturated aqueous sodium bicarbonate, and brine. The organic layer was dried over sodium sulfate, filtered, and evaporated to dryness in vacuo. The residue was chromatographed on silica gel eluted with 10% ethyl acetate in hexane, and the product fractions were evaporated to dryness in vacuo to give methyl 2-hydroxy-4-(1-Boc-4-piperidyloxy)benzoate.

Methyl 2-hydroxy-4-(1-Boc-4-piperidyloxy)benzoate (6.7 g, 19.1 mmol) was dissolved in THF (20 ml) and stirred in an ice bath under nitrogen. Sodium hydride (1.17g of a 60% suspension in mineral oil, 29.5 mmol) was added and the mixture was stirred for 15 min in the cold, then for 15 min at ambient temperature. Iodomethane (2.4 ml, 5.47 g, 38.1 mmol) was added and the mixture was allowed to stir at ambient temperature under nitrogen for 72 hours. An additional 0.51 g of 60% sodium hydride suspension was added and the mixture stirred an additional 7 hours, then an additional 1.2 ml of iodomethane was added and the mixture stirred another 18 hours. An additional 0.53 g of sodium hydride suspension was added, the mixture was stirred 1.5 hours, then an additional 1 ml of iodomethane was added and the mixture stirred 6 hours. An additional 1 ml of iodomethane was added and the mixture stirred 18 hours at ambient temperature. The mixture was diluted with ethyl acetate and washed with saturated aqueous sodium bicarbonate and with brine. The organic layer was dried over sodium sulfate, filtered, and evaporated to dryness in vacuo to give methyl 2-methoxy-4-(1-Boc-4-piperidyloxy)-benzoate.

Methyl 2-methoxy-4-(1-Boc-4-piperidyloxy)benzoate (4.5 g, 12.3 mmol) was dissolved in THF (200 ml) and treated with a solution of lithium hydroxide (17 ml of a 1.1M aqueous solution, 18.7 mmol) added over 5 min. The mixture was stirred at ambient temperature for 72 hours. An additional 4 ml of 1.1M lithium hydroxide was added and the mixture was heated at reflux for 13 hours, then stirred at ambient temperature for 18 hours. The reaction mixture was concentrated in vacuo and the residue partitioned between ethyl acetate and 1N hydrochloric acid. The organic layer was washed with brine, dried over sodium sulfate, filtered, and evaporated to dryness in vacuo to give 2-methoxy-4-(1-Boc-4-piperidyloxy)benzoic acid.

2-Methoxy-4-(1-Boc-4-piperidyloxy)benzoic acid (0.79 g, 2.24 mmol) was dissolved in ethyl acetate (15 ml). The solution was cooled in ice and saturated with HCl gas, then stirred 30 min in the cold. The mixture was evaporated in vacuo and the residue concentrated from ether three times to give 2-methoxy-4-(4-piperidyloxy)benzoic acid.

2-Methoxy-4-(4-piperidyloxy)benzoic acid (0.6 g, 2.09 mmol) was stirred in THF (10 ml) and treated with triethylamine (0.29 ml, 0.21 g, 2.08 mmol), followed by acetyl chloride (0.18 ml, 0.2 g, 2.5 mmol) and an additional 0.35 ml of triethylamine. The mixture was stirred at ambient temperature for 18 hours, then concentrated in vacuo. The residue was partitioned between aqueous sodium bicarbonate and ethyl acetate. The ethyl acetate layer was extracted with sodium bicarbonate solution. The combined sodium bicarbonate layers were acidified with 1N HCl and extracted with ethyl acetate. The organic layers were combined, washed with brine, dried over sodium sulfate, filtered, and evaporated to dryness in vacuo to give 2-methoxy-4-(1-acetyl-4-piperidyloxy)benzoic acid.

2-Methoxy-4-(1-acetyl-4-piperidyloxy)benzoic acid (0.546 g, 1.86 mmol) in THF (10 ml) was stirred under nitrogen and treated with thionyl chloride (0.27 ml, 0.44 g, 3.7 mmol). The mixture was stirred at ambient temperature for 18 hours, then concentrated in vacuo to give 2-methoxy-4-(1-acetyl-4-piperidyloxy)benzoyl chloride.

A mixture of ether (14 ml) and 40% aqueous potassium hydroxide (4.2 ml) was cooled in ice. N-Nitrosomethylurea (1.4g) was added in portions with gentle swirling over 30 min. The ether layer was decanted and dried over solid potassium hydroxide for 15 min. The ether solution was decanted, then cooled in an ice bath. A solution of 2-methoxy-4-(1-acetyl-4-piperidyloxy)benzoyl chloride (0.58 g, 1.86 mmol) in THF (3 ml) was added dropwise and the mixture was stirred at ambient temperature for 2 hours. Nitrogen was passed through the mixture for 1 hour, and the solution was then concentrated in vacuo. The residue was dissolved in methanol and treated with freshly prepared silver oxide (48 mg), and the mixture was heated at reflux for 30 min. Three additional lots of 100 mg of silver oxide were added with 1 hour reflux following each. The mixture was cooled and filtered, and the filtrate was concentrated in vacuo. The residue was chromatographed on silica gel eluted with 2%, followed by 4% methanol in methylene chloride. The product fractions were combined and evaporated to dryness in vacuo to give methyl 2-methoxy-4-(1-acetyl-4-piperidyloxy)phenylacetate.

Methyl 2-methoxy-4-(1-acetyl-4-piperidyloxy) phenylacetate (0.18 g, 0.56 mmol) was dissolved in THF (5 ml) and treated with lithium hydroxide (0.67 ml of a 1M aqueous solution, 0.67 mmol). The mixture was stirred at ambient temperature for 4 hours, then treated with an additional 0.2 ml of 1M lithium hydroxide. The mixture was heated at 60° for 6 hours, then cooled and concentrated in vacuo. The residue was acidified with 1M HCl, and extracted with ethyl acetate. The combined ethyl acetate layers were extracted with saturated aqueous sodium carbonate. The combined sodium carbonate layers were acidified with concentrated HCl and extracted with ethyl acetate. The combined ethyl acetate layers were dried over sodium sulfate, filtered, and evaporated to dryness in vacuo to give 2-methoxy-4-(1-acetyl-4-piperidyloxy)phenyl-acetic acid.

2-Methoxy-4-(1-acetyl-4-piperidyloxy)phenylacetic acid (35 mg, 0.11 mmol), 4-(2-methylphenyl)piperazine-2-carboxamide (25 mg, 0.11 mmol), EDC (28 mg, 0.15 mmol), and HBT (17 mg, 0.13 mmol) were combined in DMF (4 ml) under nitrogen. The mixture was rendered basic by addition of triethylamine (0.043 ml) and stirred at ambient temperature for 18 hours. The mixture was concentrated in vacuo and the residue was chromatographed on silica gel eluted with 2% methanol in methylene chloride. The combined product fractions were evaporated to dryness in vacuo and the residue was rechromatographed on silica gel eluted with 96:4:0.4 methylene chloride:methanol:concentrated ammonia. The combined product fractions were evaporated to dryness in vacuo and the residue was concentrated from methanol and ether to give 1-(2-methoxy-4-(1-acetyl-4-piperidyloxy)phenylacetyl)-4-(2-methylphenyl)-piperazine-2-carboxamide.

¹H-NMR: Consistent with structure

TLC: silica gel, 5% methanol in methylene chloride: single component, R$_f$=0.42

FABMS: M+H @ m/e=509

HPLC: 92%

Anal. cal'd for $C_{28}H_{36}N_4O_5 \cdot 0.9\ H_2O$: C, 64.07; H, 7.26; N, 10.68. Found: C, 63.87; H, 7.00; N, 10.59.

EXAMPLE 10

1-(2-Methoxy-4-(4-piperidyloxy)phenylacetyl)-4-(2-methylphenyl)piperazine-2-carboxamide dihydrochloride

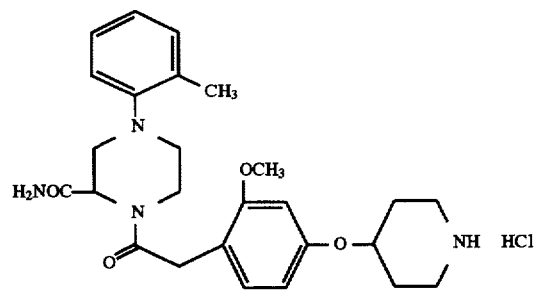

2-Methoxy-4-(1-Boc-4-piperidyloxy)benzoic acid (3.2 g, 9.1 mmol) was dissolved in THF (35 ml). Thionyl chloride (1 ml, 1.63 g, 13.7 mmol) was added dropwise, followed by 2 drops of pyridine. The mixture was stirred at ambient temperature under nitrogen for 4.5 hours, then concentrated in vacuo. The residue was reconcentrated from ether to give 2-methoxy-4-(1-Boc-4-piperidyloxy)benzoyl chloride.

A mixture of ether (66 ml) and 40% aqueous potassium hydroxide (20 ml) was cooled in ice. N-Nitrosomethylurea (6.6g) was added in portions with gentle swirling over 30 min. The ether layer was decanted and dried over solid potassium hydroxide for 15 min. The ether solution was decanted, and the decanted solution was cooled in an ice bath. A solution of 2-methoxy-4-(1-Boc-4-piperidyloxy) benzoyl chloride (3.26 g, 8.8 mmol) in THF (6 ml) was added dropwise and the mixture was stirred in the cold for 15 min and at ambient temperature for 3.5 hours. Nitrogen was passed through the mixture for 1 hour, and the solution was then concentrated in vacuo. A portion (930 mg) of the residue was dissolved in methanol and heated to reflux, and a solution of silver benzoate (200 mg) in triethylamine (2 ml) was added in five 0.1 ml portions at intervals of eight minutes. A sixth portion was added after an additional forty minutes' reflux, and after another five minutes, a seventh portion. After a final 30 minutes' reflux, the mixture was cooled and filtered, and the filtrate was concentrated in vacuo. The residue was chromatographed on silica gel eluted with 3%, followed by 5% methanol in methylene chloride. The product fractions were combined and evaporated to dryness in vacuo to give methyl 2-methoxy-4-(1-Boc-4-piperidyloxy)-phenylaceate.

Methyl 2-methoxy-4-(1-Boc-4-piperidyloxy) phenylacetate (1.37 g, 3.6 mmol) was dissolved in THF (27 ml) and treated with lithium hydroxide (4.5 ml of a 1M aqueous solution, 4.5 mmol). The mixture was stirred at ambient temperature for 4.5 hours, then treated with an additional 0.9 ml of 1M lithium hydroxide and stirred at ambient temperature for 18 hours. The mixture was concentrated in vacuo, and the residue was acidified with 1M HCl, and extracted with ethyl acetate. The combined ethyl acetate layers were dried over sodium sulfate, filtered, and evaporated to dryness in vacuo. The residue was reconcentrated from ether to give 2-methoxy-4-(1-Boc-4-piperidyloxy) phenylacetic acid.

2-Methoxy-4-(1-Boc-4-piperidyloxy)phenylacetic acid (331 mg, 0.91 mmol), 4-(2-methylphenyl)piperazine-2-carboxamide (200 mg, 0.91 mmol), EDC (209 mg, 1.09 mmol), and HBT (141 mg, 1.04 mmol) were combined in DMF (7 ml) under nitrogen. The mixture was adjusted to pH ca. 9 (moistened E. Merck colorpHast indicator) by addition of triethylamine (0.4 ml) and stirred at ambient temperature for 72 hours. The mixture was concentrated in vacuo and the residue was partitioned between ethyl acetate and aqueous sodium bicarbonate. The ethyl acetate layer was washed with sodium bicarbonate and with brine, dried over sodium sulfate, filtered, and evaporated to dryness in vacuo. The residue was chromatographed on silica gel eluted with 3% methanol in methylene chloride. The combined product fractions were evaporated to dryness in vacuo to give 1-(2-methoxy-4-(1-Boc-4-piperidyloxy)phenylacetyl)-4-(2-methylphenyl)piperazine-2-carboxamide.

1-(2-methoxy-4-(1-Boc-4-piperidyloxy)phenylacetyl)-4-(2-methylphenyl)piperazine-2-carboxamide (423 mg, 0.75 mmol) was stirred in ethyl acetate (4 ml) in an ice bath under nitrogen. A cold, saturated solution (4 ml) of HCl in ethyl acetate was added and the mixture stirred in the cold for 45 min. Nitrogen gas was passed through the mixture for 1 hour, and the reaction was concentrated in vacuo. The residue was reconcentrated from methanol and from ether to give 1-(2-methoxy-4-(4-piperidyloxy)phenylacetyl)-4-(2-methylphenyl)piperazine-2-carboxamide dihydrochloride.

$^1$H-NMR: Consistent with structure

TLC: silica gel, 90: 10:1 methylene chloride:methanol:concentrated ammonia: single component, $R_f$=0.23

FABMS: M+H @ m/e=467 (free base)

HPLC: 100%

Anal. cal'd for $C_{26}H_{34}N_4O_4 \cdot 2.0HCl0.4Et_2O.9\ H_2O$: C, 56.63 H, 7.20 N, 9.57. Found: C, 56.61; H, 7.22; N, 9.36.

EXAMPLE 11

1-(2-Methoxy-4-(1-(2-(N,N-Diethylamino) ethylsulfonyl)-4-piperidyloxy)phenylacetyl)-4-(2-methylphenyl)piperazine-2-carboxamide

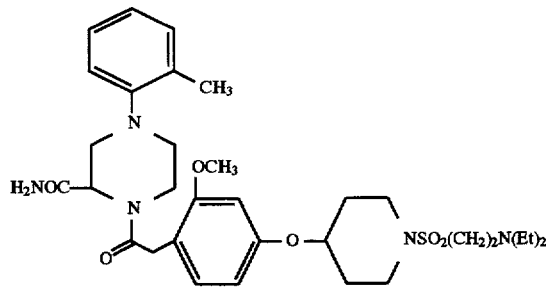

2-Chloroethanesulfonyl chloride (0.035 ml, 54.6 mg, 0.33 mmol) in methylene chloride (3 ml) was cooled in an ice bath under nitrogen. A solution of 1-(2-methoxy-4-(4-piperidyloxy)phenylacetyl)-4-(2-methylphenyl)-piperazine-2-carboxamide dihydrochloride (149 mg, 0.28 mmol) and diisopropylethylamine (0.243 ml, 0.18 g, 1.4 mmol) in methylene chloride (3 ml) was added dropwise and the mixture was stirred in the cold for 18 hours. The mixture was concentrated in vacuo and the residue chromatographed on silica gel eluted with 3% methanol in methylene chloride. The combined product fractions were evaporated to dryness in vacuo to give 1-(2-methoxy-4(1-ethenylsulfonyl-4-piperidyloxy)phenylacetyl)-4-(2-methylphenyl)piperazine-2-carboxamide.

1-(2-Methoxy-4-(1-ethenylsulfonyl-4-piperidyloxy) phenylacetyl)-4-(2-methylphenyl)piperazine-2-carboxamide (52 mg, 0.093 mmol) was dissolved in methanol (5 ml), treated with diethylamine (0.013 ml, 9.2 mg, 0.12 mmol), and stirred at ambient temperature under nitrogen for 18 hours. An additional 0.01 ml of diethylamine was added and the mixture stirred another 24 hours at ambient temperature. The reaction was concentrated in vacuo and the residue was chromatographed on silica gel eluted with 3% followed by 5%, then 7% methanol in methylene chloride. The combined product fractions were evaporated to dryness in vacuo to give 1-(2-methoxy-4-(1-(2-(N,N-diethylamino) -ethylsulfonyl)-4-piperidyloxy)phenylacetyl)-4-(2-methylphenyl)piperazine-2-carboxamide: mp 70°–140° C.

$^1$H-NMR: Consistent with structure

TLC: silica gel, 5% methanol in methylene chloride: single component, $R_f$=0.30

FABMS: M+H @ m/e=630

HPLC: 97%

Anal. cal'd for $C_{32}H_{47}N_5O_6S \cdot 0.25Et_2O.3\ H_2O$: C, 60.62; H, 7.27; N, 10.71. Found: C, 60.62; H, 7.49; N, 10.63.

EXAMPLE 12

1-(2-Methoxy-4-(1-(2-(N-cyclopropylamino)-ethylsulfonyl)-4-piperidyloxy)phenylacetyl)-4-(2-methylphenyl)piperazine-2-carboxamide

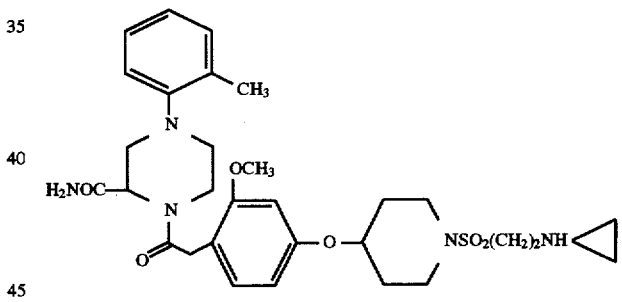

1-(2-Methoxy-4-(1-ethenylsulfonyl-4-piperidyloxy) phenylacetyl)-4-(2-methylphenyl)piperazine-2-carboxamide (69 mg, 0.12 mmol) was dissolved in methanol (4 ml), treated with cyclopropylamine (0.0072 ml, 10 mg, 0.18 mmol), and stirred at ambient temperature under nitrogen for 18 hours. An additional 0.014 ml of cyclopropylamine was added and the mixture stirred another 72 hours at ambient temperature. The reaction was concentrated in vacuo and the residue was chromatographed on silica gel eluted with 4% methanol in methylene chloride. The combined product fractions were evaporated to dryness in vacuo. The residue was reconcentrated from ether to give 1-(2-methoxy-4-(1-(2-(N-cyclopropylamino)ethylsulfonyl)-4-piperidyloxy)phenylacetyl)-4-(2-methylphenyl)piperazine-2-carboxamide: mp 69°–110° C.

$^1$H-NMR: Consistent with structure

TLC: silica gel, 5% methanol in methylene chloride: single component, $R_f$=0.35

FABMS: M+H @ m/e=614

HPLC: 97%

Anal. cal'd for $C_{31}H_{43}N_5O_6S \cdot 0.4Et_2O \cdot 0.15 H_2O$: C, 60.59; H, 7.38; N, 10.84. Found: C, 60.56; H, 7.26; N, 10.72.

EXAMPLE 13

1-(2-Methoxy-4-(-1-(3-ethoxy-3-cyclobutene-1,2-dion-4-yl)-4-piperidyloxy)phenylacetyl)-4-(2-methylphenyl) piperazine-2-carboxamide

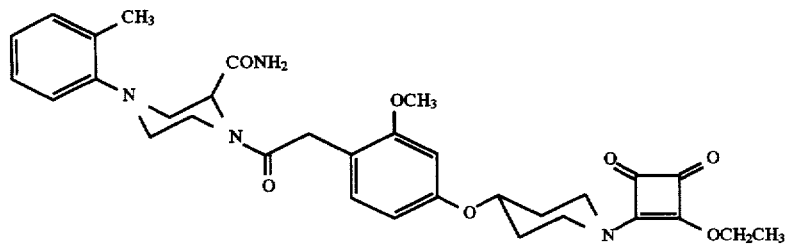

1-(2-Methoxy-4-(4-piperidyloxy)phenylacetyl)-4-(2-methylphenyl) piperazine-2-carboxamide (128 mg, 0.274 mmole) was dissolved in 4 ml of absolute ethanol. 3,4-Diethoxy-3-cyclobutene-1,2-dione (62 mg, 0.364 mmole), prepared according to the procedure in *Angew. Chem. Int. Ed.* 1966, 5(10), 890, was then added to the solution and the resulting reaction mixture was heated to reflux for 72 hr. The reaction mixture was cooled and filtered. The filter cake was washed with cold ethanol and dried to give the title compound as a white solid: m.p. 155°–157° C.

¹HNMR: Consistent with structure and confirms solvate;

TLC: $R_f$=0.46 (9:1 chloroform-methanol), single component;

HPLC: >96% (214 nM);

FABMS: 591 ($M^+$+H);

Elemental Analysis calculated, for ($C_{32}H_{35}N_3O_8 \cdot 0.6 H_2O$): Calc'd: C, 64.00; H, 6.08; N, 7.00. Found: C, 64.04; H, 5.98; N, 7.14.

EXAMPLE 14

1-(2-Methoxy-4-(1-(3-hydroxy-3-cyclobutene-1,2-dion-4-y)-4-piperidyloxy)phenylacetyl)-4-(2-methylphenyl)piperazine-2-carboxamide

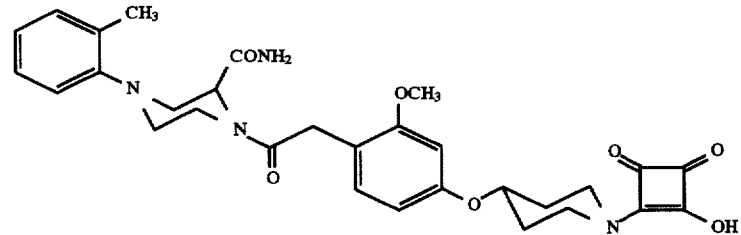

1-(2-Methoxy-4-(1-(3-ethoxy-3-cyclobutene-1,2-dion-4-yl)-4-piperidyloxy)phenylacetyl)-4-(2-methylphenyl) piperazine-2-carboxamide (87 mg, 0.147 mmole) was dissolved in 3 ml of ethanol, treated with one equivalent of 1N sodium hydroxide solution, and stirred at ambient temperature overnight. All volatiles were removed under reduced pressure and the residual material was applied directly to precoated silica gel plates (0.5 mm thickness). Multiple elutions with a chloroform-methanol-acetic acid solvent mixture (80:20:2) afforded the title compound as a white solid: m.p. 144°–148° C.

¹HNMR: Consistent with structure and confirms solvate;

TLC: $R_f$=0.29 (80:20:2 chloroform-methanol-acetic acid);

HPLC: >97% (214 nM);

FABMS: 563 ($M^+$+H), 585 ($M^+$+Na);

Elemental Analysis, calculated for ($C_{30}H_{31}N_3O_8 \cdot 1.45CHCl_3$): Calc'd: C, 51.41; H, 4.45; N, 5.72. Found: C, 51.57; H, 4.83; N, 5.55.

EXAMPLE 15

1-(2-Methoxy-4-(-1-((pyrid-3-yl)methyl)-4-piperidyloxy)phenylacetyl)-4-(2-methylphenyl) piperazine-2-carboxamide

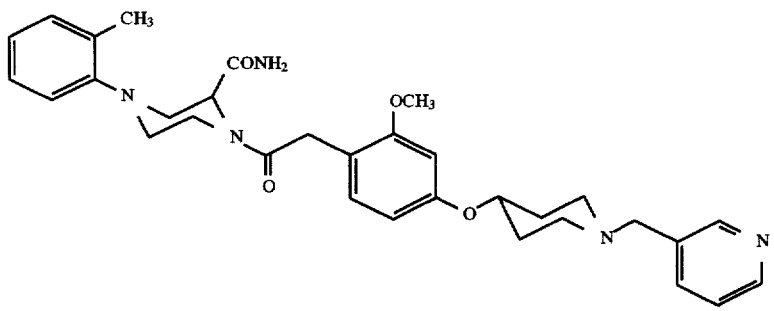

1-(2-Methoxy-4-(4-piperidyloxy)phenylacetyl)-4-(2-methylphenyl) piperazine-2-carboxamide (110 mg, 0.236 mmole) was dissolved in 3 ml of dry N,N-dimethylformamide. To this solution was added 86 μL (0.496 mmole) of diisopropylethylamine (DIEA) and 43 mg (0.26 mmole) of picolyl chloride. The reaction mixture was stirred at ambient temperature overnight and then was treated with an additional 20 mg of picolyl chloride. The pH of the reaction mixture was adjusted to 9 with DIEA and stirring was continued for 24 hr more. All volatiles were removed under reduced pressure and the residual material was partitioned between ethyl acetate and water. The organic phase was washed with 5% sodium carbonate solution and brine, then dried and concentrated. The crude product mixture was purified via preparative thick layer chromatography on precoated silica gel plates (80:20 chloroform-methanol elution) to give the title compound in homogeneous form: m.p. 78°–81° C.

$^1$HNMR: Consistent with structure and confirms solvate;

TLC: $R_f$=0.20 (90:10 chloroform-methanol);

HPLC: >98% (214 nM);

FABMS: 558 (M$^+$+H);

Elemental Analysis, calculated for ($C_{32}H_{39}N_5O_4$·0.75CHCl$_3$): Calc'd: C, 60.77; H, 6.19; N, 10.82. Found: C, 60.99; H, 6.34; N, 10.84.

EXAMPLE 16

1-(2-Methoxy-4-(1-((imidazol-4-yl)methylcarbonyl)-4-piperidyloxy)phenylacetyl)-4-(2-methylphenyl) piperazine-2-carboxamide

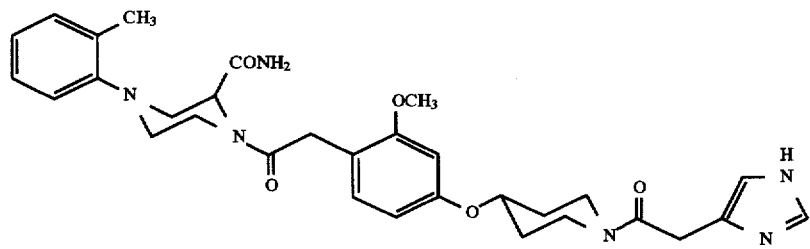

1-(2-Methoxy-4-(4-piperidyloxy)phenylacetyl)-4-(2-methylphenyl) piperazine-2-carboxamide (200 mg, 0.429 mmole) and 4-imidazoleacetic acid (70 mg, 0.429 mmole) were dissolved in 4 ml of dry N,N-dimethylformamide at room temperature. To this solution was added 209 mg (0.472 mmole) of benzotriazol-1-yloxy-tris(dimethylamino)-phosphonium hexafluorophosphate (BOP). The pH of the reaction mixture was adjusted to 9 with the addition of diisopropylethylamine (DEA) in 100 μL increments. The reaction mixture was stirred at ambient temperature for 2 hr whereupon all volatiles were removed under reduced pressure. The residue was suspended in ethyl acetate and this suspension was washed with water. The organic phase and some insoluble material were combined, concentrated, and azeotropically dried with toluene. The resulting semi-solid was purified via preparative thick layer chromatography on precoated silica gel plates (85:15:1.5 chloroform-methanol-concentrated ammonium hydroxide elution) to give the title compound in homogeneous form: m.p. 120°–124° C.

$^1$HNMR: Consistent with structure and confirms solvate;

TLC: $R_f$=0.50 (80:20:2 chloroform-methanol-conc. ammonium hydroxide);

HPLC: >95% (214 nM);

FABMS: 575 (M$^+$+H);

Elemental Analysis, calculated for ($C_{31}H_{38}N_6O_5$·1.25CHCl$_3$): Calc'd: C, 53.50; H, 5.47; N, 11.61. Found: C, 53.42; H, 5.70; N, 11.43.

EXAMPLE 17

1-Benzyl-3-Ethoxycarbonylmethyl-4-(2-methylphenyl)piperazin-2-one

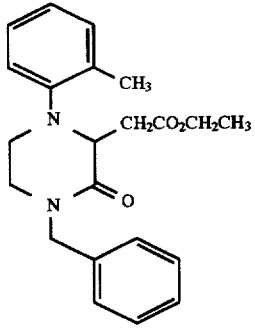

Step 1: N-Benzyl-N-(2-(2-methylphenylamino)ethyl-3-(ethoxycarbonyl)acrylamide

To a stirred solution of N-benzyl-N'-(2-methylphenyl)-1,2-diaminoethane hydrochloride (10 g; 0.036 mol; prepared by the method given in Example 5), ethyl fumarate (5.7 g; 0.040 mol), and EDC (8.3 g; 0.043 mol) in DMF (200 mL) was added DIEA (13.8 mL; 0.0792 mol) dropwise over a period of 30 minutes. The resulting mixture was stirred at ambient temperature for 18 h. The solvent was removed under reduced pressure and the residue was partitioned between EtOAc and saturated aqueous NaHCO₃. The organic phase was separated and washed with 5% aqueous citric acid, saturated aqueous NaHCO₃, and brine. The organic phase was dried (MgSO₄), filtered and evaporated under reduced pressure. The residue was purified by pressurized silica gel column chromatography using 1:3 EtOAc:hexanes as eluant. The title compound was obtained as a yellow oil (HPLC retention time 9.60 min).

1-Benzyl-3-Ethoxycarbonylmethyl-4-(2-methylphenyl) piperazin-2-one N-Benzyl-N-(2-(2-methylphenylamino)ethyl-3-(ethoxycarbonyl)acrylamide (10 g, 0.027 mol) was refluxed in 10:1 EtOH:HOAc (150 mL) for 24 h to give a 3:5 mixture of two products, HPLC retention times 8.47 min and 11.0 min, and TLC $R_f$ values of 15 0.33 and 0.20 (1:3 EtOAc:hexanes), respectively. The solvents were removed under reduced pressure and the residue was purified by pressurized silica gel column chromatography using a gradient elution of 20–30% EtOAc:hexanes. The title compound (higher TLC $R_f$, longer HPLC retention time, major product) was obtained as a colorless oil.

¹H-NMR: Consistent with structure

TLC: silica gel, 1:3 EtOAc:hexanes: single component, $R_f$=0.33

FABMS: M+H @ m/e=367

HPLC: retention time 11.0 min; >99%

EXAMPLE 18

1-Benzyl-2-Ethoxycarbonylmethyl-4-(2-methylphenyl)piperazin-3-one

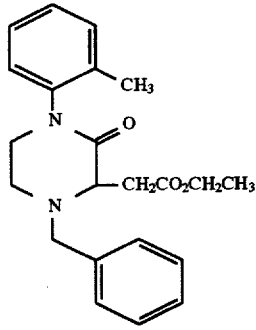

The slower eluting isomer from the chromatographic separation in Step 2 of Example 17 was isolated. The title compound (lower TLC $R_f$, shorter HPLC retention time, minor product from Step 2 of Example 17) was obtained as a colorless oil.

¹H-NMR: Consistent with structure

TLC: silica gel, 1:3 EtOAc:hexanes: single component, $R_f$=0.20

FABMS: M+H @ m/e=367

HPLC: retention time 8.47 min; >99%

EXAMPLE 19

1-(4-(t-Butyloxycarbonylamino)phenylacetyl)-3-(2-hydroxyethyl)-4-(2-methylphenyl)piperazine

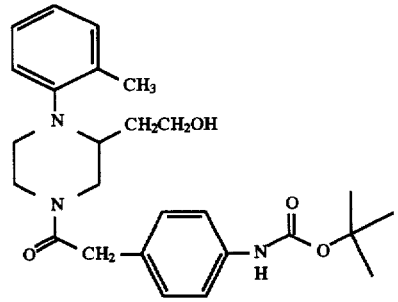

Step 1: 1-Benzyl-3-(2-hydroxyethyl)-4-(2-methylphenyl)piperazine

1-Benzyl-3-ethoxycarbonylmethyl-4-(2-methylphenyl)piperazin-2-one from Example 17 (2.5 g; 6.8 mmol) in dry THF (25 mL) was added dropwise to a stirred, 0° C. solution of LAH in THF (27 mL of a 1.0M solution; 27 mmol). The reaction was stirred at 0° C. for 1 h and then at ambient temperature for 18 h. The reaction was diluted with ether (50 mL), cooled to 0° C., and then quenched by the slow dropwise addition of 5N aqueous NaOH. The resulting suspension was stirred at ambient temperature for 1 h and filtered through Celite. The filtercake was washed with 1:1 THF:EtOAc. The filtrate solvents were evaporated under reduced pressure and the residue was purified by pressurized silica gel column chromatography using a gradient elution of 1–4% MeOH:CH₂Cl₂. The title compound was obtained as an oil (¹H-NMR: consistent with structure; TLC: silica gel, 4% MeOH:CH₂Cl₂: single component, $R_f$=0.45; FABMS: M+H @ m/e=311; HPLC: 99%, retention time 9.81 min).

Step 2: 3-(2-Hydroxyethyl)-4-(2-methylphenyl)piperazine

1-Benzyl-3-(2-hydroxyethyl)-4-(2-methylphenyl)piperazine from Step 1 above (1.5 g; 4.8 mmol) in 50 mL of MeOH containing 150 mg of palladium black was shaken on a Parr apparatus under an atmosphere of hydrogen (55 psig) for 18 h. The catalyst was removed by filtration through Celite and the filtercake was washed with MeOH. The filtrate solvents were evaporated under reduced pressure to give the title compound as an oil ($^1$H-NMR: consistent with structure; FABMS: M+H @ m/e=221; HPLC: 97%, retention time 5.20 min).

Step 3: 1-(4-(t-Butyloxycarbonylamino)phenylacetyl)-3-(2-hydroxyethyl)-4-(2-methylphenyly)piperazine To a stirred solution of 3-(2-hydroxyethyl)-4-(2-methylphenyl)piperazine from Step 2 above (0.300 g; 1.36 mmol), 4-(t-butyloxycarbonylamino)phenylacetic acid (0.342 g; 1.50 mmol), HOBT (0.18 g; 1.5 mmol), and EDC (0.315 g; 1.64 mmol) in DMF (30 mL) was added DIEA (0.29 mL; 1.7 mmol). The reaction was stirred at ambient temperature for 18 h and the solvent was evaporated under reduced pressure. The residue was partitioned between EtOAc and saturated aqueous NaHCO$_3$. The organic phase was separated and washed with saturated aqueous NaHCO$_3$ and brine. The organic phase was dried (MgSO$_4$), filtered, and the solvent was evaporated under reduced pressure. The residue was purified by pressurized silica gel column chromatography using 2:1 EtOAc:hexanes as eluant. Evaporation of a CH$_2$Cl$_2$ solution of the title compound under reduced pressure gave an amorphous solid.

$^1$H-NMR: Consistent with structure

TLC: silica gel, 3:1 EtOAc:hexanes: single component, R$_f$=0.40

FABMS: M+H @ m/e=454

HPLC: >99%, retention time 9.08 min

Anal. cal'd for C$_{26}$H$_{35}$N$_3$O$_4$·0.4 H$_2$O: C, 67.77; H, 7.83; N, 9.19 Found: C, 67.61; H, 7.64; N, 9.14

EXAMPLE 20

1-(4-(t-Butyloxycarbonylamino)phenylacetyl)-2-(2-hydroxyethyl-4-(2-methylphenyl)piperazine

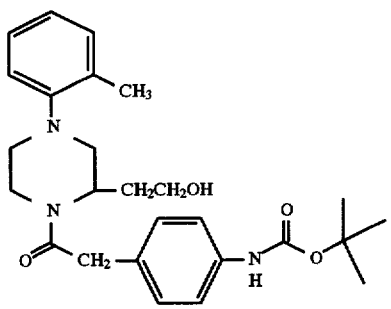

Step 1: 1-Benzyl-2-(2-hydroxyethyl)-4-(2-methylphenyl)piperazine

1-Benzyl-2-ethoxycarbonylmethyl-4-(2-methylphenyl)piperazin-8-one from Example 18 (5.0 g; 14 mmol) in dry THF (50 mL) was added dropwise to a stirred, 0° C. solution of LAH in THF (56 mL of a 1.0M solution; 56 mmol). The reaction was stirred at 0° C. for 1 h and then at ambient temperature for 18 h. The reaction was diluted with ether (100 mL), cooled to 0° C., and then quenched by the slow dropwise addition of 5N aqueous NaOH. The resulting suspension was stirred at ambient temperature for 1 h and filtered through Celite. The filtercake was washed with 1:1 THF:EtOAc. The filtrate solvents were evaporated under reduced pressure and the residue was purified by pressurized silica gel column chromatography using a gradient elution of 1–4% MeOH:CH$_2$Cl$_2$. The title compound was obtained as an oil ($^1$H-NMR: consistent with structure; TLC: silica gel, 3% MeOH:CH$_2$Cl$_2$: single component, R$_f$=0.42; FABMS: M+H @ m/e=311; HPLC: 99%, retention time 9.98 min).

Step 2: 2-(2-Hydroxyethyl)-4-(2-methylphenyl)piperazine

1-Benzyl-2-(2-hydroxyethyl)-4-(2-methylphenyl)piperazine from Step 1 above (3.2 g; 10 mmol) in 50 mL of MeOH containing 150 mg of palladium black was shaken on a Parr apparatus under an atmosphere of hydrogen (55 psig) for 18 h. The catalyst was removed by filtration through Celite and the filtercake was washed with MeOH. The filtrate solvents were evaporated under reduced pressure to give the title compound as an oil ($^1$H-NMR: consistent with structure; FABMS: M+H @ m/e=221; HPLC: 98%, retention time 5.38 min).

Step 3: 1-(4-(t-Butyloxycarbonylamino)phenylacetyl)-2-(2hydroxyethyl)-4-(2-methylphenyl)piperazine To a stirred solution of 2-(2-hydroxyethyl)-4-(2-methylphenyl)piperazine from Step 2 above (0.40 g; 1.82 mmol), 4-(t-butyloxycarbonylamino)phenylacetic acid (0.502 g; 2.00 mmol), HOBT (0.27 g; 2.0 mmol), and EDC (0.419 g; 2.18 mmol) in DMF (40 mL) was added DIEA (0.44 mL; 2.5 mmol). The reaction was stirred at ambient temperature for 18 h and the solvent was evaporated under reduced pressure. The residue was partitioned between EtOAc and saturated aqueous NaHCO$_3$. The organic phase was separated and washed with saturated aqueous NaHCO$_3$ and brine. The organic phase was dried (MgSO$_4$), filtered, and the solvent was evaporated under reduced pressure. The residue was purified by pressurized silica gel column chromatography using 2:1 EtOAc:hexanes as eluant. Evaporation of a CH$_2$Cl$_2$ solution of the title compound under reduced pressure gave an amorphous solid.

$^1$H-NMR: Consistent with structure

TLC: silica gel, 1:1 EtOAc:hexanes: single component, R$_f$=0.16

FABMS: M+H @ m/e=454

HPLC: 99%, retention time 9.99 min

Anal. cal'd for C$_{26}$H$_{35}$N$_3$O$_4$·0.8 H$_2$O: C, 66.73; H, 7.88; N, 8.98 Found: C, 66.76; H, 7.59; N, 9.97

EXAMPLE 21

1-(4-(5-Benzimidazolylcarbonylamino)phenylacetyl)-2-(2-hydroxyethyl)-4-(2-methylphenyl)piperazine

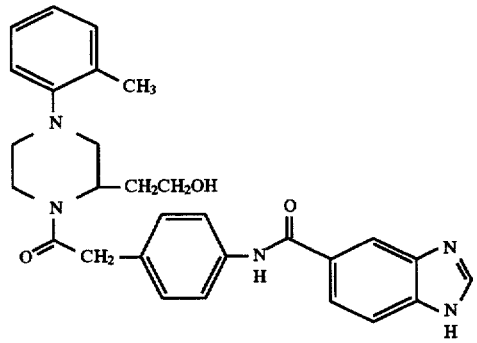

To a stirred solution of 2-(2-hydroxyethyl)-4-(2-methylphenyl)piperazine from Step 2 of Example 20 (0.20 g; 0.91 mmol), 4-(5-benzimidazolylcarbonylamino) phenylacetic acid (0.299 g; 1.00 mmol), HOBT (0.14 g; 1.0 mmol), and EDC (0.210 g; 1.09 mmol) in DMF (30 mL) was added DIEA (0.23 mL; 1.3 mmol). The reaction was stirred at ambient temperature for 18 h and the solvent was evaporated under reduced pressure. The residue was partitioned between $CH_2Cl_2$ and saturated aqueous $NaHCO_3$. The organic phase was separated and washed with saturated aqueous $NaHCO_3$ and brine. The organic phase was dried ($MgSO_4$), filtered, and the solvent was evaporated under reduced pressure. The residue was purified by pressurized silica gel column chromatography using 95:5:0.5 $CH_2Cl_2$:MeOH:$NH_4OH$ as eluant. Trituration in EtOAc gave the title compound as an amorphous solid.

$^1$H-NMR: Consistent with structure

TLC: silica gel, 92:8:0.4 $CH_2Cl_2$:MeOH:$NH_4OH$: single component, $R_f$=0.35

FABMS: M+H @ m/e=498

HPLC: 99%, retention time 7.25 min

Anal. cal'd for $C_{29}H_{31}N_5O_3$·1.0 $H_2O$·0.09 EtOAc: C, 67.36; H, 6.49; N, 13.38 Found: C, 67.52; H, 6.51; N, 13.38

EXAMPLE 22

1-(4-(5-Benzimidazolylcarbonylamino)phenyl-acetyl)-2-(2-methoxyethyl-4-(2-methylphenyl) piperazine

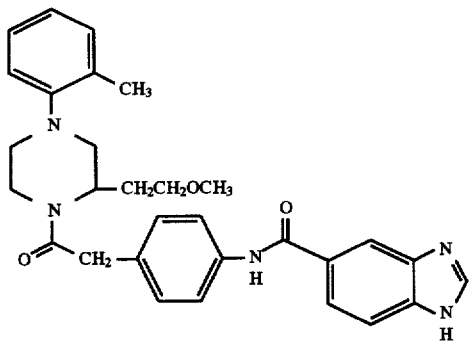

Step 1: 1-t-Butyloxycarbonyl-2-(2-hydroxyethyl)-4-(2-methylphenyl)piperazine

To a stirred solution of 2-(2-hydroxyethyl)-4-(2-methylphenyl)piperazine from Step 2 of Example 20 (2.0 g; 9.1 mmol) in DMF (50 mL) was added di-t-butyl dicarbonate (2.1 g; 9.6 mmol). The reaction was stirred at ambient temperature for 18 h and the solvent was evaporated under reduced pressure. The residue was purified by pressurized silica gel column chromatography using 1:4 EtOAc:hexanes as eluant. The title compound was obtained as a gum ($^1$H-NMR: consistent with structure; TLC: silica gel, 1:3 EtOAc:hexanes: single component, $R_f$=0.33; FABMS: M+H @ m/e=321; HPLC: >99%, retention time 9.88 min).

Step 2: 1-t-Butyloxycarbonyl-2-(2-methoxyethyl)-4-(2-methylphenyl)-piperazine

To a stirred, 0° C. solution of 1-t-butyloxycarbonyl-2-(2-hydroxyethyl)-4-(2-methylphenyl)piperazine from Step 1 above (0.38 g; 1.2 mmol) and iodomethane (0.20 mL; 3.4 mmol) in dry THF (20 mL) was added NaH (60 mg of a 60% suspension in mineral oil; 1.5 mmol). The reaction was stirred at 0° C. for 15 min and then at ambient temperature for 18 h. The reaction was quenched by adding several drops of MeOH and the solvents were evaporated under reduced pressure. The residue was partitioned between EtOAc and water. The organic phase was separated and washed with water and brine. The organic phase was dried ($MgSO_4$), filtered, and the solvent was removed under reduced pressure. The residue was purified by pressurized silica gel column chromatography using 1:4 EtOAc:hexanes as eluant. The title compound was obtained as a gum ($^1$H-NMR: consistent with structure; TLC: silica gel, 1:3 EtOAc:hexanes: single component, $R_f$=0.62; FABMS: M+H @ m/e=335; HPLC: >99%, retention time 11.7 min).

Step 3: 2-(2-methoxyethyl)-4-(2-methylphenyl)piperazine hydrochloride

Through a stirred, 0° C. solution of 1-t-butyloxycarbonyl-2-(2-methoxyethyl)-4-(2-methylphenyl)piperazine from Step 2 above (0.350 g; 1.05 mmol) in dry EtOAc (40 mL) was bubbled HCl gas for 20 min. The reaction was stirred at 0° C. for 15 min and then at ambient temperature for 30 min. The solvent was evaporated under reduced pressure to give the title compound as an amorphous solid ($^1$H-NMR: consistent with structure; HPLC: >99%, retention time 6.18 min).

Step 4: 1-(4-(5-Benzimidazolylcarbonylamino) phenylacetyl)-2-(2-methoxyethyl-4-(2-methylphenyl) piperazine To a stirred solution of 2-(2-methoxyethyl)-4-(2-methylphenyl)piperazine hydrochloride from Step 3 above (0.25 g, 0.92 mmol), 4-(5-benzimidazolylcarbonylamino) phenylacetic acid (0.299 g; 1.00 mmol), HOBT (0.14 g; 1.0 mmol), and EDC (0.210 g; 1.09 mmol) in DMF (30 mL) was added DIEA (0.23 mL; 1.3 mmol). The reaction was stirred at ambient temperature for 18 h and the solvent was evaporated under reduced pressure. The residue was partitioned between $CH_2Cl_2$ and saturated aqueous $NaHCO_3$. The organic phase was separated and washed with saturated aqueous $NaHCO_3$ and brine. The organic phase was dried ($MgSO_4$), filtered, and the solvent was evaporated under reduced pressure. The residue was purified by pressurized silica gel column chromatography using 95:5:0.5 $CH_2Cl_2$:MeOH:$NH_4OH$ as eluant. Evaporation of a $CH_2Cl_2$ solution of the title compound under reduced pressure gave an amorphous solid.

$^1$H-NMR: Consistent with structure

TLC: silica gel, 93:7:0.35 $CH_2Cl_2$:MeOH:$NH_4OH$: single component, $R_f$=0.26

FABMS: M+H @ m/e=512

HPLC: 98.7%, retention time 8.04 min

Anal. cal'd for $C_{30}H_{33}N_5O_3$·1.0 $H_2O$: C, 68.03; H, 6.66; N, 13.22 Found: C, 68.05; H, 6.77; N, 13.17

EXAMPLE 23

1-(4-(5-Benzimidazolylcarbonylamino)phenyl-acetyl)-2-(2-methylthioethyl-4-(2-methylphenyl) piperazine

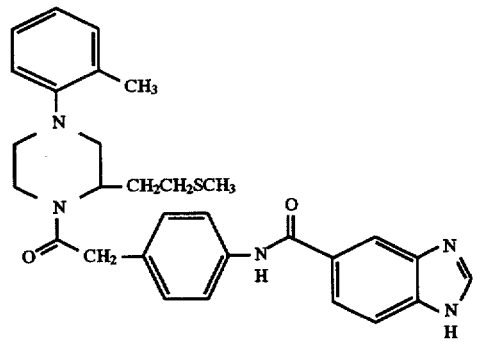

Step 1: 1-t-Butyloxycarbonyl-2-(2-methylsulfonyloxy-ethyl)-4-(2-methylphenyl)piperazine To a stirred, 0° C. solution of 1-t-butyloxycarbonyl-2-(2-hydroxyethyl)-4-(2-methylphenyl)piperazine from Step 1 of Example 22 (0.32 g; 1.0 mmol) and DIEA (0.35 mL; 2.0 mmol) in dry $CH_2Cl_2$ (10 mL) was added methanesulfonyl chloride (0.085 mL; 1.1 mmol). The reaction was stirred at 0° C. for 15 min and then at ambient temperature for 5 h. The solvent was evaporated under reduced pressure and the residue was partitioned between EtOAc and water. The organic phase was separated and washed with water and brine. The organic phase was dried ($MgSO_4$), filtered, the solvent was removed under reduced pressure and the title compound, obtained as a gum, was used directly in the next step.

Step 2: 1-t-Butyloxycarbonyl-2-(2-methylthioethyl)-4-(2methylphenyl)piperazine

A stirred solution of -1-t-butyloxycarbonyl-2-(2-methylsulfonyloxyethyl)-4-(2-methylphenyl)piperazine from Step I above (0.39 g; 0.98 mmol) and sodium thiomethoxide (0.21 g; 3.0 mmol) in dry THF (15 mL) was heated to reflux for 18 h. The solvent was evaporated under reduced pressure and the residue was partitioned between EtOAc and water. The organic phase was separated and washed with saturated aqueous $NaHCO_3$ and brine. The organic layer was dried ($MgSO_4$), filtered, and the solvent was evaporated under reduced pressure. The residue was purified by pressurized silica gel column chromatography using 1:4 EtOAc:hexanes as eluant. The title compound was isolated as a gum ($^1$H-NMR: consistent with structure; TLC: silica gel, 1:4 EtOAc:hexanes: single component, $R_f$=0.50; FABMS: M+H @ m/e=351; HPLC: >99%, retention time 12.0 min).

Step 3: 2-(2-Methylthioethyl)-4-(2-methylphenyl)piperazine hydrochloride

Through a stirred, 0° C. solution of 1-t-butyloxycarbonyl-2-(2-methylthioethyl)-4-(2-methylphenyl)piperazine from Step 2 above (0.30 g; 0.86 mmol) in dry EtOAc (40 mL) was bubbled HCl gas for 20 min. The reaction was stirred at 0° C. for 15 min and then at ambient temperature for 30 min. The solvent was evaporated under reduced pressure to give the title compound as an amorphous solid ($^1$H-NMR: consistent with structure; HPLC: >99%, retention time 6.39 min).

Step 4: 1-(4-(5-Benzimidazolylcarbonylamino)phenylacetyl)-2-(2-methylthioethyl-4-(2-methylphenyl)piperazine To a stirred solution of 2-(2-methylthioethyl)-4-(2-methylphenyl)piperazine hydrochloride from Step 3 above (0.25 g, 0.87 mmol), 4-(5-benzimidazolylcarbonylamino)phenylacetic acid (0.282 g; 0.96 mmol), HOBT (0.14 g; 1.0 mmol), and EDC (0.192 g; 1.00 mmol) in DMF (30 mL) was added DIEA (0.21 mL; 1.2 mmol). The reaction was stirred at ambient temperature for 18 h and the solvent was evaporated under reduced pressure. The residue was partitioned between $CH_2Cl_2$ and saturated aqueous $NaHCO_3$. The organic phase was separated and washed with saturated aqueous $NaHCO_3$ and brine. The organic phase was dried ($MgSO_4$), filtered, and the solvent was evaporated under reduced pressure. The residue was purified by pressurized silica gel column chromatography using 95:5:0.5 $CH_2Cl_2$:MeOH:$NH_4OH$ as eluant. Evaporation of a $CH_2Cl_2$ solution of the title compound under reduced pressure gave an amorphous solid.

$^1$H-NMR: Consistent with structure
TLC: silica gel, 90:10:0.5 $CH_2Cl_2$:MeOH:$NH_4OH$: single component, $R_f$=0.47
FABMS: M+H @ m/e=528
HPLC: 97%, retention time 8.42 min Anal. cal'd for $C_{30}H_{33}N_5O_2S \cdot 1.5 H_2O$: C, 64.96; H, 6.54; N, 12.63 Found: C, 65.01; H, 6.16; N, 12.36

EXAMPLE 24

1-(4-(5-Benzimidazolylcarbonylamino)phenylacetyl)-2-(2-azidoethyl)-4-(2-methylphenyl)piperazine

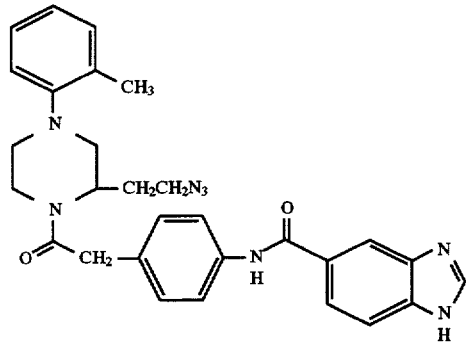

Step 1: 1-t-Butyloxycarbonyl-2-(2-azidoethyl)-4-(2-methylphenyl)piperazine

A stirred solution of -1-t-butyloxycarbonyl-2-(2-methylsulfonyloxyethyl)-4-(2-methylphenyl)piperazine from Step I of Example 23 (0.40 g; 1.0 mmol) and sodium azide (0.30 g; 4.6 mmol) in dry DMF (15 mL) was heated to 60° C. for 18 h. The solvent was evaporated under reduced pressure and the residue was partitioned between EtOAc and water. The organic phase was separated and washed with saturated aqueous $NaHCO_3$ and brine. The organic layer was dried ($MgSO_4$), filtered, and the solvent was evaporated under reduced pressure. The residue was purified by pressurized silica gel column chromatography using 1:9 EtOAc:hexanes as eluant. The title compound was isolated as a gum ($^1$H-NMR: consistent with structure; TLC: silica gel, 1:9 EtOAc:hexanes: single component, $R_f$=0.50; FABMS: M+H @ m/e=346; HPLC: >99%, retention time 12.4 min).

Step 2: 2-(2-Azidoethyl)-4-(2-methylphenyl)piperazine hydrochloride

Through a stirred, 0° C. solution of 1-t-butyloxycarbonyl-2-(2-azidoethyl)-4-(2-methylphenyl)piperazine from Step 1 above (0.29 g; 0.84 mmol) in dry EtOAc (40 mL) was bubbled HCl gas for 20 min. The reaction was stirred at 0° C. for 15 min and then at ambient temperature for 30 min. The solvent was evaporated under reduced pressure to give the title compound as an amorphous solid ($^1$H-NMR: consistent with structure; HPLC: >99%, retention time 6.43 min).

Step 3: 1-(4-(5-Benzimidazolylcarbonylamino)phenylacetyl)-2-(2-azidoethyl-4-(2-methylphenyl)piperazine To a stirred solution of 2-(2-azidoethyl)-4-(2-methylphenyl)-piperazine hydrochloride from Step 3 above (0.24 g, 0.85 mmol), 4-(5-benzimidazolylcarbonylamino)phenylacetic acid (0.277 g; 0.94 mmol), HOBT (0.14 g; 1.0 mmol), and EDC (0.192 g; 1.00 mmol) in DMF (30 mL) was added DIEA (0.21 mL; 1.2 mmol). The reaction was stirred at ambient temperature for 18 h and the solvent was evaporated under reduced pressure. The residue was partitioned between $CH_2Cl_2$ and saturated aqueous $NaHCO_3$. The organic phase was separated and washed with saturated aqueous $NaHCO_3$ and brine. The organic phase was dried ($MgSO_4$), filtered, and the solvent was evaporated under reduced pressure. The residue was purified by pressurized silica gel column chromatography using 95:5:0.5 CH$_2$Cl$_2$:MeOH:NH$_4$OH as eluant. Evaporation of a CH$_2$Cl$_2$ solution of the title compound under reduced pressure gave an amorphous solid.

$^1$H-NMR: Consistent with structure

TLC: silica gel, 90:10:0.5 CH$_2$Cl$_2$:MeOH:NH$_4$OH: single component, R$_f$=0.54

FABMS: M+H @ m/e=523

HPLC: >99%, retention time 8.38 min

Anal. cal'd for C$_{29}$H$_{30}$N$_8$O$_2$.0.33 CH$_2$Cl$_2$: C, 63.98; H, 5.61; N, 20.35 Found: C, 63.85; H, 5.65; N, 20.31

EXAMPLE 25

1-(4-(5-Benzimidazolylcarbonylamino)phenyl-acetyl)-2-(2-aminoethyl)-4-(2-methylphenyl)piperazine

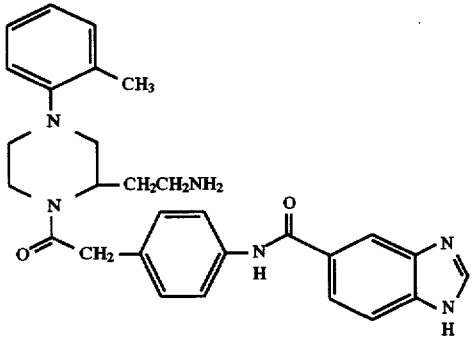

A solution of 1-(4-(5-benzimidazolylcarbonylamino)phenylacetyl)-2-(2-azidoethyl-4-(2-methylphenyl)piperazine from Example 24 (0.24 g, 0.46 mmol) and triphenylphosphine (0.235 g; 0.90 mmol) in 10:1 THF:H$_2$O was stirred at ambient temperature for 48 h. The solvents were removed under reduced pressure and the residue was partitioned between EtOAc and brine. The organic phase was dried (MgSO$_4$), filtered, and the solvent was evaporated under reduced pressure. The residue was purified by preparative reverse phase HPLC using an H$_2$O:CH$_3$CN gradient containing 0.1% TFA. The TFA salt of the title compound was obtained as an amorphous powder by lyophilization.

$^1$H-NMR: Consistent with structure

TLC: silica gel, 90:10:0.5 CH$_2$Cl$_2$:MeOH:NH$_4$OH: single component, R$_f$=0.14

FABMS: M+H @ m/e=497

HPLC: >99%, retention time 6.09 min

Anal. cal'd for C$_{29}$H$_{32}$N$_6$O$_2$.2.45 TFA.0.55 H$_2$O: C, 51.81; H, 4.56; N, 10.69 Found: C, 51.80; H, 4.55; N, 11.00

EXAMPLE 26

1-(4-(5-Benzimidazolylcarbonylamino)phenyl-acetyl)-2-(2-dimethylaminoethyl-4-(2-methylphenyl)piperazine

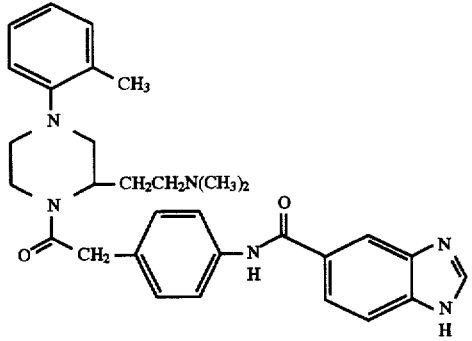

To a stirred solution of 1-(4-(5-benzimidazolylcarbonylamino)-phenylacetyl)-2-(2-aminoethyl-4-(2-methylphenyl)piperazine TFA salt from Example 25 (0.10 g, 0.20 mmol) and 37% aqueous formaldehyde (0.10 mL; 1.2 mmol) in 100:1 MeOH:HOAc (10 mL) was added NaCNBH$_3$ (76 mg; 1.2 mmol). The reaction was stirred at ambient temperature for 18 h. The solvents were removed under reduced pressure and the residue was partitioned between EtOAc and saturated aqueous NaHCO3. The organic phase was dried (MgSO$_4$), filtered, and the solvent was evaporated under reduced pressure. The residue was purified by preparative reverse phase HPLC using an H$_2$O:CH$_3$CN gradient containing 0.1% TFA. The TFA salt of the title compound was obtained as an amorphous powder by lyophilization.

$^1$H-NMR: Consistent with structure

TLC: silica gel, 90:10:0.5 CH$_2$Cl$_2$:MeOH:NH$_4$OH: single component, R$_f$=0.19

FABMS: M+H @ m/e=525

HPLC: 95%, retention time 6.39 min

Anal. cal'd for C$_{31}$H$_{36}$N$_6$O$_2$.1.8 TFA.1.5 H$_2$O: C, 54.90; H, 5.43; N, 11.10 Found: C, 54.93; H, 5.47; N, 10.90

EXAMPLE 27

1-(4-(5-Benzimidazolylcarbonylamino)phenyl-acetyl)-2-(2-methylsulfonyl-ethyl-4-(2-methylphenyl)piperazine

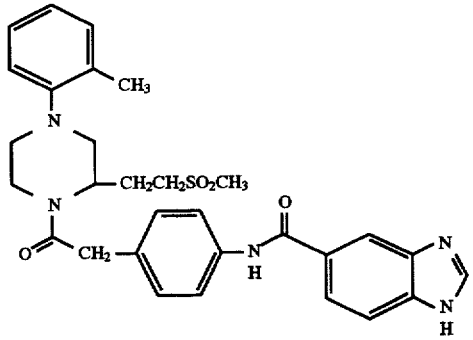

A solution of 1-(4-(5-benzimidazolylcarbonylamino)phenylacetyl)-2-(2-methylthioethyl)-4-(2-methylphenyl)

piperazine from Example 23 (0.10 g, 0.19 mmol), N-methylmorpholine-N-oxide (110 mg; 0.95 mmol) and $OsO_4$ (0.20 mL of a 4 wt. % solution in water; 0.031 mmol) in 10:1 acetone:water (5 mL) was stirred at ambient temperature for 72 h. The solvents were removed under reduced pressure and the residue was purified by preparative reverse phase HPLC using an $H_2O:CH_3CN$ gradient containing 0.1 % TFA. The TFA salt of the title compound was obtained as an amorphous powder by lyophilization.

$^1$H-NMR: Consistent with structure

TLC: silica gel, 95:5:0.5 $CH_2Cl_2$:MeOH:$NH_4OH$: single component, $R_f$=0.13

FABMS: M+H @ m/e=560

HPLC: 98%, retention time 7.18 min

Anal. cal'd for $C_{30}H_{38}N_5O_4S.1.55$ TFA.1.4 $H_2O$: C, 52.19; H, 4.94; N, 9.20 Found: C, 52.20; H, 4.64; N, 9.59

EXAMPLE 28

1-(4-(5-Benzimidazolylcarbonylamino)phenyl-acetyl)-4-(2-ethylphenyl)piperazine

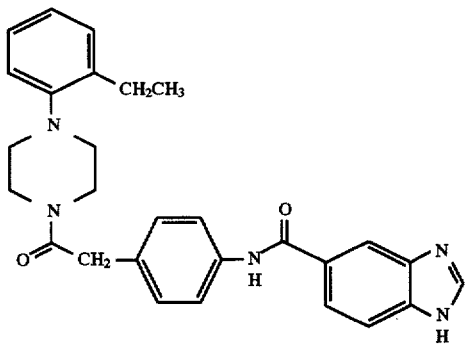

To a stirred solution of 1-(2-ethylphenyl)piperazine (0.19 g; 1.0 mmol), 4-(5-benzimidazolylcarbonylamino) phenylacetic acid (0.329 g; 1.10 mmol), HOBT (0.14 g; 1.0 mmol), and EDC (0.230 g; 1.20 mmol) in DMF (30 mL) was added DIEA (0.23 mL; 1.3 mmol). The reaction was stirred at ambient temperature for 18 h and the solvent was evaporated under reduced pressure. The residue was partitioned between $CH_2Cl_2$ and saturated aqueous $NaHCO_3$. The organic phase was separated and washed with saturated aqueous $NaHCO_3$ and brine. The organic phase was dried ($MgSO_4$), filtered, and the solvent was evaporated under reduced pressure. The residue was purified by pressurized silica gel column chromatography using 93:7:0.35 $CH_2Cl_2$:MeOH:$NH_4OH$ as eluant. Evaporation of the product-containing fractions under reduced pressure gave the title compound as an amorphous solid.

$^1$H-NMR: Consistent with structure

TLC: silica gel, 90:10:0.5 $CH_2Cl_2$:MeOH:$NH_4OH$: single component, $R_f$=0.38

FABMS: M+H @ m/e=468

HPLC: 99%, retention time 7.33 min

Anal. cal'd for $C_{28}H_{29}N_5O_2.0.3$ $CH_2Cl_2$: C, 68.94; H, 6.05; N, 14.20 Found: C, 69.08; H, 7.73; N, 14.19

EXAMPLE 29

1-(4-(5-Benzimidazolylcarbonylamino)phenyl-acetyl)-4-(2-chlorophenyl)piperazine

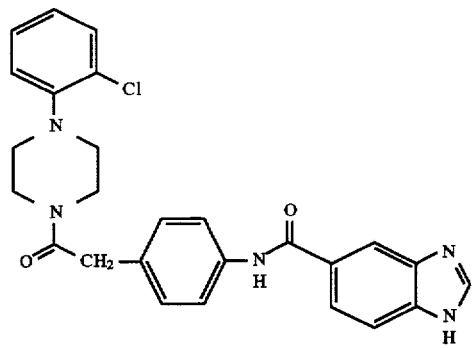

To a stirred solution of 1-(2-chlorophenyl)piperazine (0.20 g; 1.0 mmol), 4-(5-benzimidazolylcarbonylamino) phenylacetic acid (0.329 g; 1.10 mmol), HOBT (0.14 g; 1.0 mmol), and EDC (0.230 g; 1.20 mmol) in DMF (30 mL) was added DIEA (0.23 mL; 1.3 mmol). The reaction was stirred at ambient temperature for 18 h and the solvent was evaporated under reduced pressure. The residue was partitioned between $CH_2Cl_2$ and saturated aqueous $NaHCO_3$. The organic phase was separated and washed with saturated aqueous $NaHCO_3$ and brine. The organic phase was dried ($MgSO_4$), filtered, and the solvent was evaporated under reduced pressure. The residue was purified by preparative reverse phase HPLC using an $H_2O:CH_3CN$ gradient containing 0.1 % TFA. Lyophilization of the product-containing fractions gave the TFA salt of the title compound as an amorphous solid.

$^1$H-NMR: Consistent with structure

TLC: silica gel, 90:10:0.5 $CH_2Cl_2$:MeOH:$NH_4OH$: single component, $R_f$=0.32

FABMS: M+H @ m/e=473, 475

HPLC: 99%, retention time 7.17 min

Anal. cald for $C_{26}H_{24}ClN_5O_2.1.4$ TFA.0.15 $H_2O$: C, 54.36; H, 4.07; N, 11.01 Found: C, 54.33; H, 4.05; N, 11.11

EXAMPLE 30

1-(4-(5-Benzimidazolylcarbonylamino)phenyl-acetyl)-4-(2-methoxyphenyl)piperazine

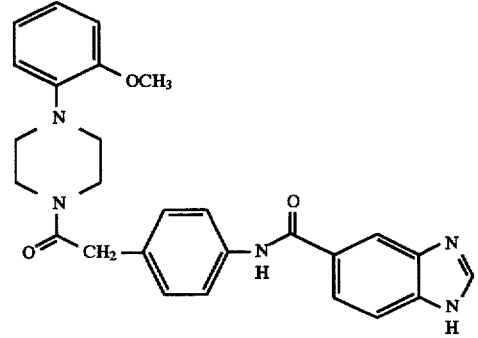

To a stirred solution of 1-(2-methoxyphenyl)piperazine (0.19 g; 1.0 mmol), 4-(5-benzimidazolylcarbonylamino) phenylacetic acid (0.329 g; 1.10 mmol), HOBT (0.14 g; 1.0 mmol), and EDC (0.230 g; 1.20 mmol) in DMF (30 mL) was added DIEA (0.23 mL; 1.3 mmol). The reaction was stirred at ambient temperature for 18 h and the solvent was evaporated under reduced pressure. The residue was partitioned between CH$_2$Cl$_2$ and saturated aqueous NaHCO$_3$. The organic phase was separated and washed with saturated aqueous NaHCO$_3$ and brine. The organic phase was dried (MgSO$_4$), filtered, and the solvent was evaporated under reduced pressure. The residue was purified by preparative reverse phase HPLC using an H$_2$O:CH$_3$CN gradient containing 0.1% TFA. Lyophilization of the product-containing fractions gave the TFA salt of the title compound as an amorphous solid.

$^1$H-NMR: Consistent with structure

TLC: silica gel, 90:10:0.5 CH$_2$Cl$_2$:MeOH:NH$_4$OH: single component, R$_f$=0.33

FABMS: M+H @ m/e=470

HPLC: 99%, retention time 4.73 min

Anal. cal'd for C$_{27}$H$_{27}$N$_5$O$_3$.2.05 TFA.0.4 H$_2$O: C, 52.57; H, 4.23; N, 9.86 Found: C, 52.57; H, 4.19; N, 9.88

EXAMPLE 31

1-(4-(5-Benzimidazolylcarbonylamino)phenyl-acetyl)-4-(2,6-dimethylphenyl)piperazine

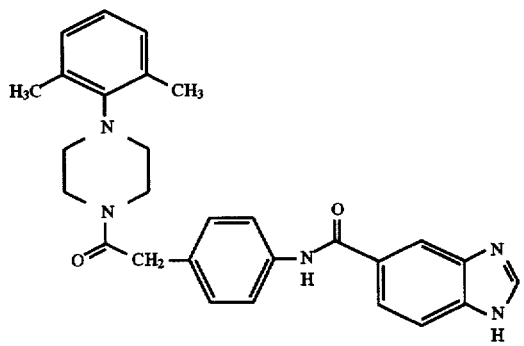

To a stirred solution of 1-(2,6-dimethylphenyl)piperazine (0.19 g; 1.0 mmol), 4-(5-benzimidazolylcarbonylamino) phenylacetic acid (0.329 g; 1.10 mmol), HOBT (0.14 g; 1.0 mmol), and EDC (0.230 g; 1.20 mmol) in DMF (30 mL) was added DIEA (0.23 mL; 1.3 mmol).

The reaction was stirred at ambient temperature for 18 h and the solvent was evaporated under reduced pressure. The residue was partitioned between CH$_2$Cl$_2$ and saturated aqueous NaHCO$_3$. The organic phase was separated and washed with saturated aqueous NaHCO$_3$ and brine. The organic phase was dried (MgSO$_4$), filtered, and the solvent was evaporated under reduced pressure. The residue was purified by pressurized silica gel column chromatography using 93:7:0.35 CH$_2$Cl$_2$:MeOH:NH$_4$OH as eluant. Evaporation of the product-containing fractions under reduced pressure gave the title compound as an amorphous solid.

$^1$H-NMR: Consistent with structure

TLC: silica gel, 90:10:0.5 CH$_2$Cl$_2$:MeOH:NH$_4$OH: single component, R$_f$=0.38

FABMS: M+H @ m/e=468

HPLC: 99%, retention time 7.75 min

Anal. cal'd for C$_{28}$H$_{29}$N$_5$O$_2$.0.76 H$_2$O: C, 69.88; H, 6.39; N, 14.55 Found: C, 69.87; H, 6.08; N, 14.39

EXAMPLE 32

As a specific embodiment of an oral composition of a compound of this invention, 100 mg of the compound of Example 5 is formulated with sufficient finely divided lactose to provide a total amount of 580 to 590 mg to fill a size 0 hard gel capsule.

EXAMPLE 33

RADIOLIGAND BINDING ASSAYS

The high affinity binding of [$^3$H]oxytocin (OT) to uterine tissue and [$^3$H]arginine vasopressin (AVP) to liver (AVP-VI site) and kidney (AVP-V$_2$ site) tissue was determined using crude membrane preparations as described previously [Pettibone, D. J., et al., J. Pharmacol. and Exper. Ther., 256(1): 304–308 (1991)]. Uterine tissue was taken from nonpregnant adult Sprague-Dawley rats (Taconic Farms, Germantown, N.Y.) pretreated (18–24 h) with diethylstilbestrol propionate (DES; 300 µg/kg, i.p.). Uterine tissue (full thickness) was also taken with informed consent from nonlabor pregnant women undergoing cesarean section at 38 to 39 weeks gestation (Oregon Health Sciences Center, Portland, Oreg.). Liver and kidney medulla samples were taken from male rats and from human surgical and early postmortem donors (National Disease Research Interchange, Philadelphia Pa.; Analytical Biological Services, Wilmington, Del.).

Competition studies were conducted at equilibrium using 1 nM [$^3$H]OT or 0.5 nM [$^3$H]AVP in the following buffer: 50 mM Tris, 5 mM MgCl$_2$, 0.1 % bovine serum albumin. Nonspecific binding was determined using 1 µM unlabeled OT or AVP in their respective assays. The binding reactions were initiated by the addition of tissue preparation and terminated by filtration using a Skatron cell harvester (model 7019, Skatron, Inc., Sterling, Va.). Ki values were calculated for each compound using three to six separate IC$_{50}$ determinations (K$_i$=IC$_{50}$/[1-c/K$_d$]); [Cheng, Y.-C.; Prusoff, W. H.; Biochem Pharmacol 22:3099 (1973)] with mean Kd values obtained from replicate (n=3) equilibrium saturation binding assays (10 point, 100 fold concentration range): [$^3$H]OT rat uterus, 0.69 nM; human myometrium, 1.1 nM; [$^3$H]AVP: rat liver, 0.21 nM; rat kidney, 0.27 nM; human liver, 0.27 nM; human kidney, 1.4 nM. Computer analysis of the saturation assays by EBDA/LIGAND [McPherson, G. A.: Kinetic, Ebda, Ligand, Lowry: A Collection of Radioligand Binding Analysis Programs, Elsevier Science Publishers, Amsterdam (1985)] indicated that both radioligands apparently bound to single sites in all tissues examined. The final protein concentration for the various tissues in each assay ranged from 150 to 300 µg/ml [Lowry, P. H.; Rosebrough, N. J.; Farr, A. L.; Randall, R. J.; J. Biol. Chem., 193:265–275 (1951)].

IC$_{50}$ values were determined for the [$^3$H]OT and [$^3$H]AVP binding assays by linear regression of the relation log concentration of compound vs. percent inhibition of specific binding. Data is either reported as a given percentage of inhibition at a specified concentration, or if an IC$_{50}$ was calculated, as a nanomolar concentration. Representative IC$_{50}$ values of the compounds of the instant invention for rat [$^3$H]OT are given below.

| Example | Result For [$^3$H]OT (nM) |
| --- | --- |
| 1 | 400 |
| 2 | 120 |
| 4 | 1600 |
| 6 | 540 |
| 7 | 80 |
| 8 | 30 |
| 9 | 34 |
| 11 | 21 |
| 12 | 20 |

-continued

| Example | Result For [³H]OT (nM) |
|---|---|
| 14 | 24 |
| 15 | 28 |

EXAMPLE 34
EXEMPLARY FUNCTIONAL ASSAYS

1. Antagonism of OT-stimulated contractions of the rat isolated uterus

As described previously [Pettibone et al., 1989], uterine horns removed from adult Sprague-Dawley rats (Taconic Farms, Germantown, N.Y.) treated 18 h earlier with DES (0.25 mg/kg, i.p.) were mounted longitudinally in standard tissue baths (30° C.) containing a physiological buffer solution and oxygenated continuously. Tissues were connected to isometric force displacement transducers and placed under a tension of 1 g. Contraction of the longitudinal muscle layer was amplified and recorded on a polygraph. A cumulative concentration-response curve was obtained using a 4 min exposure at each concentration of OT. Once the maximal effect (Emax) was attained, the tissues were washed repeatedly for 75 min. at which time antagonist or vehicle was added to the tissue bath, and 45 min later, a second concentration-response curve to OT was constructed. The concentration of OT producing 50% of $E_{max}$ before and after treatment was determined by regression analysis. Dose ratios ($EC_{50}$ after treatment/$EC_{50}$ before) were corrected, if indicated, by a factor derived from concurrent vehicle-treated tissues. The results were analyzed for competitiveness, and the $pA_2$ value was estimated from standard Schild plot [Arunlakshana and Schild, 1959].

2. OT antagonist activity in the nonpregnant rat

The procedure for measuring isometric contraction of the uterus in situ was adapted from that of Chan et al. [1974] as previously described [Pettibone et al., 1989]. Sprague-Dawley rats (200–300 g, Taconic Farms, Germantown, N.Y.) pretreated with DES (0.25 mg/kg, i.p.; 18 h) were anesthetized with urethane (1.75 g/kg, i.p.), a tracheal cannula was inserted, and a femoral vein was cannulated. The left uterine horn was exposed, and the anterior part of the horn was secured with surgical silk to an anchor post. A second ligature about 3 cm posterior to the first tie was connected to a force transducer and maintained at a tension of 1 g. Signals from the transducer were amplified and recorded. The contractile response of the uterus to OT was quantified by computerized measurement of the area under the contraction-time curve for a 10-min period immediately after the injection of OT. The following protocol was adopted for most experiments. OT (1 µg/kg; approximately an $ED_{50}$ dose) was injected i.v. every 35 min for a total of eight times. The contractile response obtained from the third injection was set as 100%. Areas determined after each injection was expressed as a percentage of the area obtained for the third injection. Fifteen min before the fourth injection of OT, vehicle or test compound was infused i.v. for 10 min. The dose of test compound required to reduce the response to OT by 50% ($AD_{50}$) was calculated from the contractile areas obtained after the fourth injection of OT (i.e., 5 min postinfusion of test compound). Percent antagonism (relative to the concurrent vehicle-treated group) was determined for each dose of test compound and $AD_{50}$ was estimated by regression analysis.

REFERENCES

Arunklaskshana O. Schild HO (1959); Some quantitative uses of drug antagonists. Br J pharmacol 14:48–58.

Pettibone D. J., Clineschmidt B. V., Anderson P. S., Freidinger R. M., Lundell G. F., Koupal L. R., Schwartz C. D., Williamson J. M., Goetz M. A., Hensens O. D., Liesch J. M., Springer J. P. (1989): A structurally unique, potent and selective oxytocin antagonist derived from *Streptomyces silvensis*. Endocrinology 125:217–222.

Chan W. Y., Nestor J. J., Ferger M. F., DuBigneaud V (1974): Inhibition of oxytocic responses to osytocin in pregnant rats by [1-L-penicillamine]-oxytocin. Proc Soc Exp Biol Med 146:364–366.

In addition to those compounds specifically exemplified above, additional compounds of the present invention are set forth in tabular form below. These compounds are synthesized by use of the synthetic routes and methods described in the above Schemes and Examples and variations thereof well known to those of ordinary skill in the art, and not requiring undue experimentation. All variables listed in the Tables below are with reference to the following generic structure:

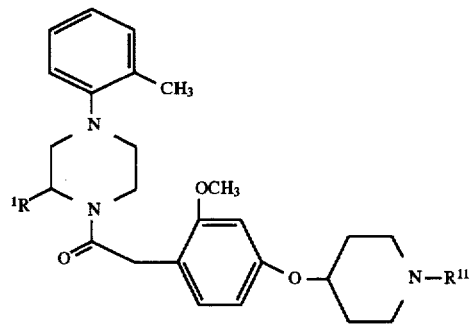

TABLE

| R' | R¹¹ |
|---|---|
| —C(O)—NH₂ | —CH₂—CH(CH₃)₃ |
| —C(O)—NH₂ | (pyridyl-CH₂-CH-C(O)- group) |
| —C(O)—NH₂ | (imidazole N—H group) |

TABLE-continued
| R' | R[11] |
|---|---|
| —C(O)—NH$_2$ | 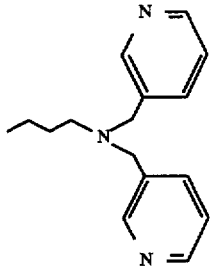 |
| —C(O)—NH$_2$ | 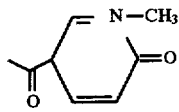 |
| —C(O)—NH$_2$ | 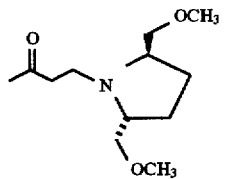 |
| —C(O)—NH$_2$ | 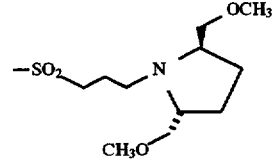 |
| —C(O)—NH$_2$ | 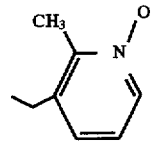 |
| —C(O)—NH$_2$ |  |
| —C(O)—NH$_2$ |  |
| —C(O)—NH$_2$ | 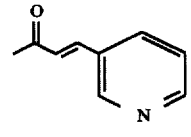 |
| —C(O)—NH$_2$ | H |
| —C(O)—NH$_2$ | 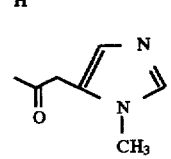 |
| —C(O)—NH$_2$ | 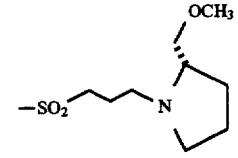 |

| R' | R[11] |
|---|---|
| —C(O)—NH$_2$ | (3-pyridyl)-CH$_2$-NH-CH$_2$-C(O)-CH$_3$ |
| —C(O)—NH$_2$ | —SO$_2$-(CH$_2$)$_3$-N(piperazine)-N-CH$_2$CH$_2$CH$_3$ |
| —C(O)—NH$_2$ | CH$_3$-C(O)-CH$_2$-N(piperazine)-N-CH$_3$ |
| —C(O)—NH$_2$ | CH$_3$-C(O)-(CH$_2$)$_3$-N(piperazine)-N-CH$_3$ |
| —C(O)—NH$_2$ | CH$_3$-C(O)-CH=C(imidazolyl) |
| —C(O)—NH$_2$ | 3-ethyl-2,4-dimethylpyridine |
| —C(O)—NH$_2$ | —SO$_2$-(CH$_2$)$_3$-NH-CH$_2$-(4-pyridyl) |
| —C(O)—NH$_2$ | —SO$_2$-(CH$_2$)$_3$-NH-CH$_2$-(3-pyridyl) |
| —C(O)—NH$_2$ | —SO$_2$-(CH$_2$)$_3$-N(piperazine)-N-CH$_3$ |
| —C(O)—NH$_2$ | 3-ethyl-2-methylpyridine |
| —C(O)—NH$_2$ | 5-ethyl-2-methoxypyridine |
| —C(O)—NH$_2$ | CH$_3$-C(O)-O-C(CH$_3$)$_3$ |
| —C(O)—NH$_2$ | 4-amino-5-nitro-6-methylpyrimidine |

TABLE-continued

| R' | R¹¹ |
|---|---|
| $-C(O)-NH_2$ | cyclopentyl with $-SO_2-$ and $N(CH_3)_2$ substituents |
| $-C(O)-NH_2$ | chloro-nitro-methyl pyrimidine |
| $-C(O)-NH_2$ | $-SO_2\text{-}(CH_2)_3\text{-}NH\text{-}C(CH_3)_3$ |
| $-C(O)-NH_2$ | methyl-nitro pyridine |
| $-C(O)-NH_2$ | $-SO_2\text{-}(CH_2)_3\text{-}NH\text{-cyclopropyl}$ |
| $-C(O)-NH_2$ | $-SO_2\text{-}(CH_2)_3\text{-}$pyrrolidinyl |
| $-C(O)-NH_2$ | $-SO_2\text{-}(CH_2)_3\text{-}N(CH_3)\text{-cyclopropyl}$ |
| diethylaminoethyl acetamide | $-C(O)-CH_3$ |
| $-C(O)-NH_2$ | $-SO_2\text{-}(CH_2)_2\text{-imidazolyl}$ |
| diethylaminoethyl acetamide | $-C(O)-O-C(CH_3)_3$ |
| $-C(O)-NH_2$ | 2,4,6-trimethylpyridine (with ethyl) |
| $-C(O)-NH_2$ | $-SO_2\text{-}(CH_2)_3\text{-}Cl$ |
| $-C(O)-NH_2$ | 3-ethylpyridine |
| $-C(O)-NH_2$ | imidazolyl ketone |

TABLE-continued
| R' | R[11] |
|---|---|
| —C(O)—NH$_2$ | (3-methyl-4-ethoxy-cyclobutene-1,2-dione) |
| —C(O)—NH$_2$ | (3-methyl-4-hydroxy-cyclobutene-1,2-dione) |
Also included within the present invention are the following compounds which can be synthesized by use of synthetic routes and methods described in the above schemes and Examples and variations thereof well known to those of ordinary skill in the art.
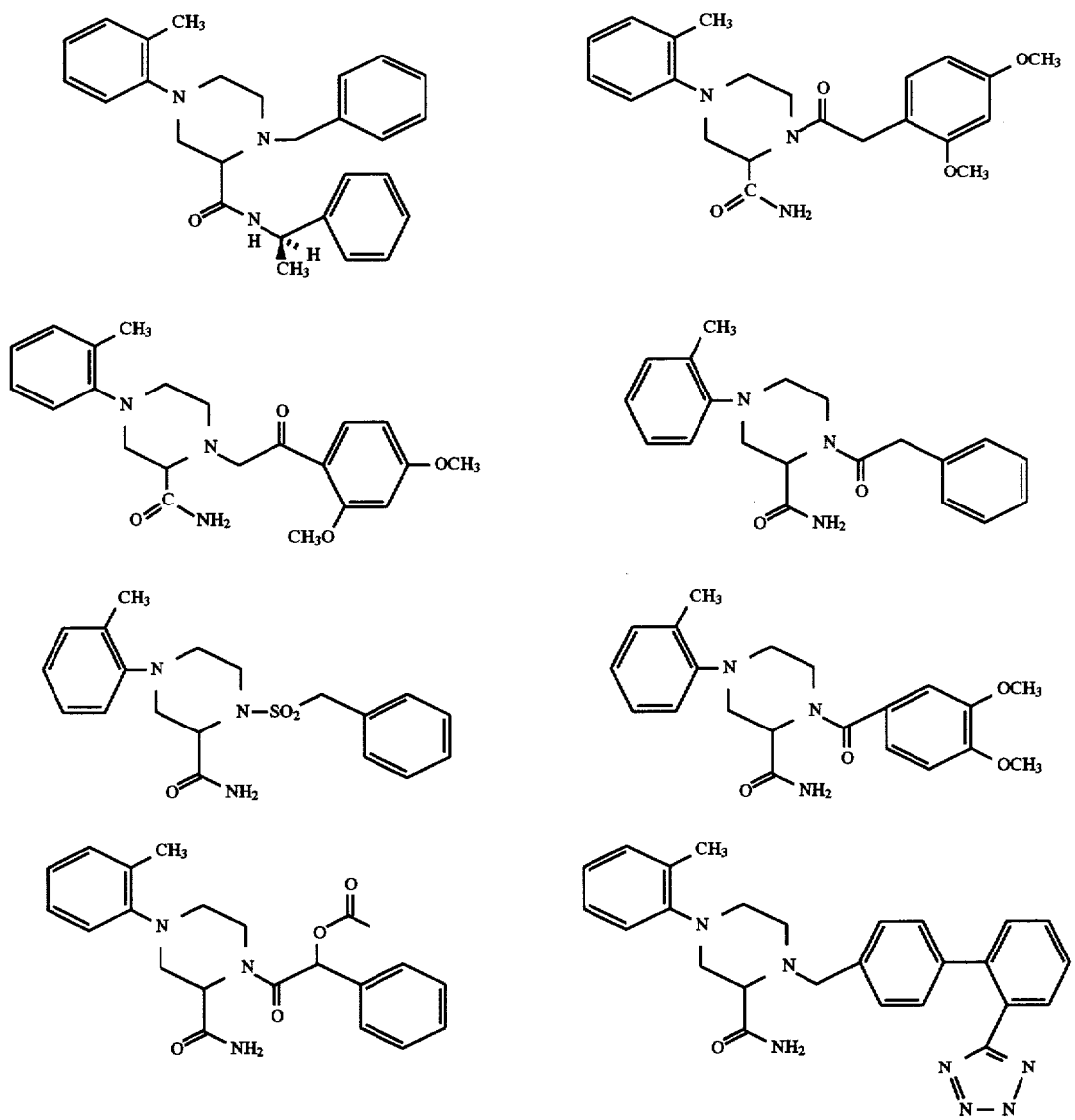

-continued

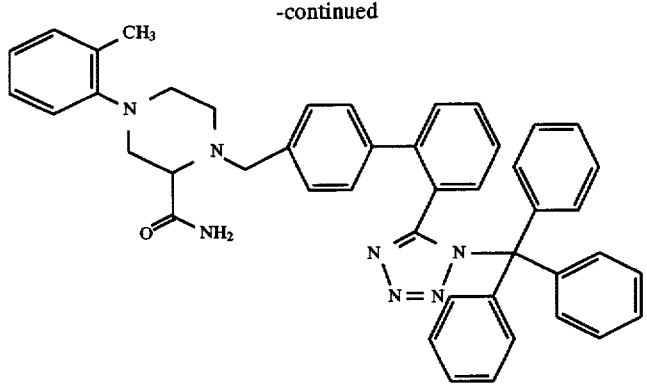

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth hereinabove may be applicable as a consequence of variations in the responsiveness of the mammal being treated for prevention of preterm labor, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of the formula X—Y—R,

X is

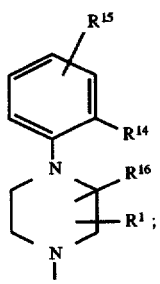

or a pharmaceutically acceptable salt thereof wherein:

Y is selected from the group consisting of;

R is unsubstituted or substituted phenyl where said substitutents are one or more of $R^5$, $R^6$ or $R^7$;

$R^1$ is selected from the group consisting of cyano, —$CONHR^2$, —$CONR^2R^2$, —$(CH_2)_p$—$S(O)_r$—$R^2$, —$(CH_2)_m$—$CO_2R^2$, —$(CH_2)_m$—$N_3$;

$R^2$ is selected from the group consisting of hydrogen, $C_{3-8}$ cycloalkyl and $C_{1-5}$ alkyl;

$R^5$ and $R^6$ are each independently selected from the group consisting of hydrogen, $C_{1-5}$ alkyl, $C_{1-5}$ alkoxy, halogen, and —$(CH_2)_n$—$N(R^2)$—$R^{17}$;

$R^7$ is selected from the group consisting of

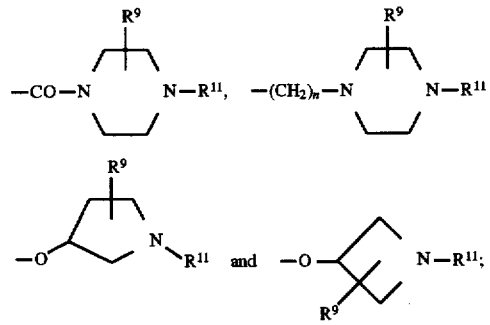

$R^9$ is hydrogen;

$R^{11}$ is selected from the group consisting of hydrogen, $C_{1-5}$ alkoxycarbonyl, $C_{1-5}$ alkylcarbonyl, $C_{1-5}$ alkyl, Z—$R^{13}$,

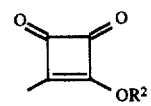

and substituted $C_{1-5}$ alkyl wherein said substituent on said alkyl is unsubstituted, mono-, di- or tri-substituted pyridyl wherein said substituents on said pyridyl are independently selected from halogen, $C_{1-5}$ alkoxyl, and $C_{1-5}$ alkyl;

$R^{13}$ is selected from the group consisting of $C_{1-10}$ alkyl, and substituted $C_{1-10}$ alkyl wherein the substituent is selected from the group consisting of —$N(R^2)_2$, and —$NHR^2$;

$R^{14}$ is selected from the group consisting of $C_{1-5}$ alkyl, $C_{1-5}$ alkoxyl, and halogen;

$R^{15}$ is selected from the group consisting of hydrogen and $C_{1-5}$ alkyl;

$R^{16}$ is selected from the group consisting of hydrogen and oxo;

$R^{17}$ is —Z—$R^{18}$;

$R^{18}$ is selected from the group consisting of $C_{1-5}$ alkoxyl, Het, unsubstituted or substituted $C_{1-5}$ alkyl wherein said substituent is Het and unsubstituted or substituted $C_{2-5}$ alkenyl wherein said substituent is Het;

Het is selected from the group consisting of imidazolyl, benzimidazolyl, carboxymethyl-substituted benzimidazolyl, indolyl;

Z is —CO— or —SO$_2$—;

m is an integer of from 1 to 5;

n is an integer of from 0 to 3;

p is an integer of from 1 to 3; and r is an integer of from 0 to 2;

2. The compound of claim 1 or a pharmaceutically acceptable salt thereof wherein.

Y is —CO—(CH$_2$)$_n$-;

R$^5$ and R$^6$ are each independently selected from the group consisting of hydrogen, C$_{1-5}$ alkoxy, halogen and —(CH$_2$)$_n$—N(R$^2$)—R$^{17}$;

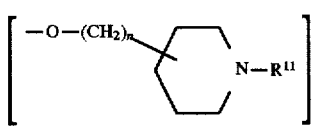

R$^{11}$ is selected from the group consisting of hydrogen, C$_{1-5}$ alkylcarbonyl, —Z—R$^{13}$,

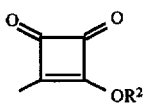

and substituted C$_{1-5}$ alkyl wherein said substituent on said alkyl is unsubstituted, mono-, di- or tri-substituted pyridyl wherein said substituents on said pyridyl are independently selected from the group consisting of halogen, C$_{1-5}$ alkyl and C$_{1-5}$ alkoxyl;

R$^{13}$ is selected from the group consisting of unsubstituted C$_{1-10}$ alkyl and substituted C$_{1-10}$ alkyl wherein said substituent is selected from the group consisting of —N(R$^2$)$_2$, and —NHR$^2$;

R$^{17}$ is —Z—R$^{18}$; and

Het is selected from the group consisting of imidazolyl, benzimidazolyl, carboxymethyl-substituted benzimidazolyl and indolyl.

3. The compound of claim 2, or a pharmaceutically acceptable salt thereof wherein

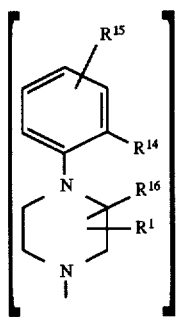

R$^1$ is selected from the group consisting of —CONHR$^2$, —(CH$_2$)$_m$— CO$_2$R$^2$, —(CH$_2$)$_p$—S(O)$_r$R$^2$, —(CH$_2$)$_m$—N$_3$.

4. A pharmaceutical composition comprising a pharmaceutically acceptable carrier and a pharmacologically effective amount of the compound as claimed in claim 1.

5. A method of eliciting an oxytocin antagonizing effect in a mammal, comprising the step of administering to said mammal a pharmacologically effective amount of the compound as claimed in claim 1.

6. A method of treating preterm labor in a mammal in need thereof, comprising the step of administering to said mammal a pharmacologically effective amount of the compound as claimed in claim 1.

7. A method of stopping labor preparatory to cesarian delivery in a mammal in need thereof, comprising the step of administering to said mammal a pharmacologically effective amount of the compound as claimed in claim 1.

8. A method of treating dysmenorrhea in a mammal in need thereof, comprising the step of administering to said mammal a pharmacologically effective amount of the compound as claimed in claim 1.

9. A method of increasing fertility and embryonic survival in a farm animal, comprising administering to the farm animal a pharmacologically effective amount of the compound of claim 1.

10. A method for improving survival of a farm animal neonate comprising controlling timing of parturition to effect delivery of the neonate during daylight hours by administering to a farm animal which is expected to deliver the neonate within 24 hours a pharmacologically effective amount of the compound of claim 1.

11. A method of controlling the timing of estrus in a farm animal, comprising administering to the farm animal a pharmacologically effective amount of the compound of claim 1.

* * * * *